United States Patent
Daniels et al.

(10) Patent No.: US 10,828,462 B2
(45) Date of Patent: Nov. 10, 2020

(54) SYSTEMS AND METHODS FOR IMPAIRING SMOOTH MUSCLE TISSUE FUNCTION

(75) Inventors: Craig E. Daniels, Rochester, MN (US); Samuel J. Asirvatham, Rochester, MN (US)

(73) Assignee: Sanovas Intellectual Property, LLC, Reno, NV (US)

( * ) Notice: Subject to any disclaimer, the term of this patent is extended or adjusted under 35 U.S.C. 154(b) by 0 days.

(21) Appl. No.: 13/375,698

(22) PCT Filed: Jun. 1, 2010

(86) PCT No.: PCT/US2010/036819
§ 371 (c)(1),
(2), (4) Date: Feb. 24, 2012

(87) PCT Pub. No.: WO2010/141417
PCT Pub. Date: Dec. 9, 2010

(65) Prior Publication Data
US 2012/0143099 A1   Jun. 7, 2012

Related U.S. Application Data

(60) Provisional application No. 61/182,811, filed on Jun. 1, 2009.

(51) Int. Cl.
*A61M 25/00* (2006.01)
*A61B 18/14* (2006.01)
*A61M 25/10* (2013.01)
*A61B 17/00* (2006.01)
*A61N 7/02* (2006.01)
(Continued)

(52) U.S. Cl.
CPC ..... *A61M 25/0029* (2013.01); *A61B 18/1492* (2013.01); *A61M 25/1011* (2013.01); *A61B 18/1815* (2013.01); *A61B 2017/00084* (2013.01); *A61B 2017/00809* (2013.01); *A61B 2017/22067* (2013.01); *A61B 2018/0022* (2013.01); *A61B 2018/00065* (2013.01); *A61B 2018/00214* (2013.01); *A61B 2018/00261* (2013.01); *A61B 2018/00285* (2013.01); *A61B 2018/00541* (2013.01); *A61B 2018/00839* (2013.01); *A61B 2018/1467* (2013.01); *A61B 2218/002* (2013.01); *A61M 2025/0681* (2013.01); *A61M 2025/1052* (2013.01); *A61M 2025/1086* (2013.01); *A61N 7/022* (2013.01)

(58) Field of Classification Search
CPC .............................. A61N 7/00; A61H 23/0245
USPC .............................................................. 601/2
See application file for complete search history.

(56) References Cited

U.S. PATENT DOCUMENTS 5,919,188 A * 7/1999 Shearon ............. A61B 18/1492
                                                              600/374
2001/0049517 A1* 12/2001 Zadno-Azizi et al. ....... 604/509
(Continued)

OTHER PUBLICATIONS

International Search Report and Written Opinion of the International Searching Authority Application No. PCT/US2010/036819 Completed: Jan. 10, 2011; dated Feb. 9, 2011 12 pages.

*Primary Examiner* — Hien N Nguyen
(74) *Attorney, Agent, or Firm* — Forge IP, PLLC

(57) ABSTRACT

Systems and methods for impairing smooth muscle tissue function using energy and/or pressure are described herein. The systems and/or methods may be used in some embodiments to target smooth muscle tissue in the bronchial passages.

13 Claims, 9 Drawing Sheets

(51) Int. Cl.
*A61B 18/00* (2006.01)
*A61M 25/06* (2006.01)
*A61B 17/22* (2006.01)
*A61B 18/18* (2006.01)

(56) References Cited

U.S. PATENT DOCUMENTS

| | | |
|---|---|---|
| 2002/0026211 A1 | 2/2002 | Khosravi et al. |
| 2002/0077643 A1* | 6/2002 | Rabiner ........... A61B 17/22012 |
| | | 606/169 |
| 2002/0099367 A1 | 7/2002 | Guo et al. |
| 2002/0138094 A1 | 9/2002 | Borillo et al. |
| 2003/0100919 A1* | 5/2003 | Hopkins et al. .............. 606/200 |
| 2004/0199156 A1* | 10/2004 | Rioux et al. ................... 606/41 |
| 2004/0230188 A1* | 11/2004 | Cioanta et al. ................. 606/34 |
| 2005/0096647 A1* | 5/2005 | Steinke .............. A61B 18/1492 |
| | | 606/41 |
| 2009/0125014 A1* | 5/2009 | Bouthillier et al. ............ 606/34 |
| 2010/0137859 A1* | 6/2010 | Wang ................. A61B 18/1492 |
| | | 606/41 |

\* cited by examiner

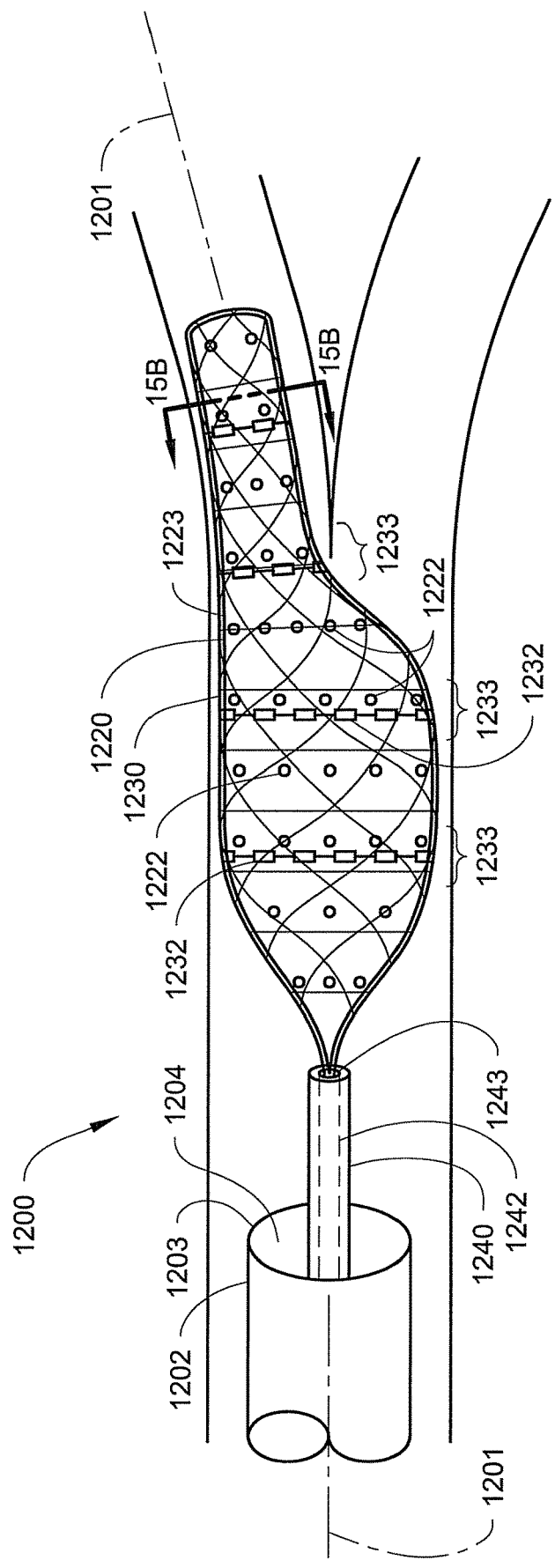

SYSTEMS AND METHODS FOR IMPAIRING SMOOTH MUSCLE TISSUE FUNCTION

RELATED APPLICATION

The present application is the § 371 U.S. National Stage of International Application No. PCT/US2010/036819, filed Jun. 1, 2010, which claims the benefit under 35 U.S.C. § 119(e) of U.S. Provisional Patent Application No. 61/182,811, filed on Jun. 1, 2009 and titled SYSTEMS AND METHODS FOR IMPAIRING SMOOTH MUSCLE TISSUE FUNCTION, which is hereby incorporated by reference in its entirety.

The systems and/or methods discussed herein may be useful, e.g., in impairing the function of smooth muscle tissue lining a variety of body cavities (where body cavities include body lumens).

Although described in connection with pulmonary applications, the systems and/or methods described herein may be used to impair functioning of the smooth muscle tissue lining the walls of a variety of different body cavities including, but not limited to: the gastrointestinal tract, hepatobiliary system, genitourinary tract, ureters, pharageal cavity, vascular spaces, arteries, veins, endolymphatic and cisternes in the intercranial space, etc. The systems may be deployed and/or used within a lumen, for example, in the common biliary duct or in the small intestine or antrum of the stomach with ablation that may either target the smooth muscle directly (management of spasm for example) or the autonomic afferent, efferent or intramyocardial neurons for indirect, as well as direct manipulation of vascular and smooth muscle tone. The systems and/or methods may also be used in specific blood vessels near autonomic fiberage structures such as the renal veins, renal arteries, pancreatic vessels and carotid body. Specific algorithms and iterations of the energy delivery system may be more applicable than another when targeting the periluminal/perivascular autonomic fibers. In some embodiments, the systems and methods described herein may be used to target intra- and/or extra-bronchial autonomics with ablation and other modalities.

When used in the pulmonary system, the systems and methods described herein may be employed to affect the functioning of airway smooth muscle (ASM) lining pulmonary cavities. Impairing smooth muscle tissue functioning in pulmonary based applications may be useful to, e.g., treat asthma in a patient.

In some embodiments, the energy may be delivered using one or more return electrodes that may be positioned intra-bronchially and/or extra-bronchially. Extra-bronchial return electrodes may be located internally within the patient, e.g., within the pleural space, etc. and/or on the skin of the patient. Some potentially useful extra-bronchial placements for return electrodes may include, e.g., in the mediastinum; individualized positioning on the skin of the patient (e.g., placing the electrode(s) behind the right lower lobe while ablating in the right middle or right lower lobe); in the azygous vein; in the superior venacava or other vascular structures; peribrochial placement (e.g., either via exiting the bronchus and/or through mediastinoscopy; etc. In some embodiments, the return electrode may also be a virtual electrode in the form of saline or other fluid provided in, e.g., the peri-bronchial and/or extra-bronchial spaces.

In some embodiments, the devices and systems described herein that use one or more return electrodes, it should be understood that the energy delivery may be revered, i.e., that the electrode (or electrodes) located intra-bronchially could function as the return electrode while energy is delivered through one or more electrodes positioned peri-bronchially and/or extra-bronchially.

Although one of the reasons for the extra-bronchial and/or pen-bronchial placement of an electrode is for smooth muscle ablation from a potentially superior vantage point, in some embodiments, extra-bronchial and/or peri-bronchial placement of electrodes and the delivery of energy using those electrodes may provide for specific manipulation, modulation and ablation of the autonomic nervous system relevant to the bronchial smooth muscle to which the energy is delivered as a part of the ablation process.

Further, in some embodiments, the systems and methods described herein may enhance targeting of the autonomic nervous system such as, e.g., the use of direct current (DC) ablation including virtual dc ablation with adjunctive alcohol or alcohol releasing radicals (which could potentially be expected to specifically injure autonomic nervous tissue while limiting damage to the smooth muscle tissue); the use of gels or other slow release preparations could be placed adjacent to the bronchus or bronchial vessels in the peri-bronchial space to produce slower or potentially longer lasting beneficial effects acting via the autonomic nervous system; the use of iontophoresis, radiofrequency (RF) energy, and/or DC energy may all potentiate activation and utility of neurolytic agents placed in the gel or effusate; etc. These neuro-modulatory techniques may also be useful in targeting the somatic nerves for pain control in addition to the effects on the autonomic nervous system.

In a first aspect, some embodiments of a smooth muscle tissue impairment system as described herein may include an elongated sheath comprising a proximal and a distal end, wherein a longitudinal axis extends between the proximal end and the distal end; fluid supply apparatus comprising a fluid reservoir and a pump; and a fluid delivery lumen extending through the sheath, wherein the fluid delivery lumen comprises an input port operably connected to the fluid supply apparatus and a delivery port proximate the distal end of the sheath, wherein fluid from the fluid reservoir can be delivered through the fluid delivery lumen to the delivery port using the fluid supply apparatus. The system may further include ablation apparatus comprising: a fluid delivery element in fluid communication with the delivery port of the fluid delivery lumen, the fluid delivery element defining a fluid volume, wherein the fluid delivery element is permeable to a fluid delivered into the fluid delivery element through the fluid delivery lumen such that the fluid can exit the fluid volume through the permeable fluid delivery element, and wherein the fluid delivery element can be moved distally and proximally relative to the sheath; and an ablation device positioned over at least a portion of the fluid delivery element, wherein the ablation device is expandable radially relative to the longitudinal axis, wherein the ablation device can be moved distally and proximally relative to the sheath, and wherein the ablation device comprises a plurality of electrodes positioned over an exterior surface of the fluid delivery element; and an energy source operably connected to the plurality of electrodes through one or more conductors extending through the sheath; wherein movement of the fluid delivery element and the ablation device distally and proximally relative to the sheath moves the plurality of electrodes distally and proximally relative to the sheath.

In some embodiments of systems according to the first aspect, the fluid delivery element comprises a bladder that is permeable through a plurality of openings formed through a wall of the bladder.

In some embodiments of systems according to the first aspect, the ablation device comprises a proximal end and a distal end, and wherein the ablation device expands to a smaller size radially proximate the distal end of the ablation device and a larger size radially proximate the proximal end of the ablation device.

In some embodiments of systems according to the first aspect, the ablation device comprises an expandable cage.

In some embodiments of systems according to the first aspect, the plurality of electrodes are distributed over the ablation device such that the number of electrodes per unit length of the ablation device decreases when moving distally along the direction of the longitudinal axis.

In some embodiments of systems according to the first aspect, the fluid delivery element and the ablation device are expandable from a compact configuration in which they are contained in a sheath lumen located in the sheath to an enlarged configuration in which the fluid delivery element and the ablation device comprise radial dimensions relative to the longitudinal axis that are larger than a radial dimension of the sheath lumen.

In some embodiments of systems according to the first aspect, a fluid return lumen may be provided, wherein the fluid return lumen comprises a return port proximate the distal end of the sheath, wherein at least a portion of fluid delivered to the fluid delivery element through the fluid delivery lumen can be removed through the fluid return lumen.

In some embodiments of systems according to the first aspect, the energy source comprises a DC electrical source, an RF energy source, an ultrasonic energy source, a microwave energy source, a vibration energy source, a laser, and/or a combination of any two or more thereof.

In some embodiments of systems according to the first aspect, the system may include a temperature sensing system comprising a temperature sensor located proximate the distal end of the sheath.

In some embodiments of systems according to the first aspect, the fluid delivery device and the ablation device are located at a distal end of a catheter, wherein the catheter, the fluid delivery device, and the ablation device are located within a sheath lumen in the sheath and movable distally along the longitudinal axis within the sheath lumen, and wherein the fluid delivery element and the ablation device are expandable from a compact configuration in which they are contained in the sheath lumen to an enlarged configuration in which the fluid delivery element and the ablation device comprise radial dimensions relative to the longitudinal axis that are larger than a radial dimension of the sheath lumen. In some embodiments, the fluid delivery lumen and the delivery port are located in the catheter. In some embodiments, the sheath is positioned in a working channel of a bronchoscope.

In a second aspect, some embodiments of a smooth muscle tissue impairment system may include an elongated sheath having a proximal and a distal end, wherein a longitudinal axis extends between the proximal end and the distal end; fluid supply apparatus including a fluid reservoir and a pump; a delivery lumen extending through the sheath, wherein the delivery lumen includes an input port operably connected to the fluid supply apparatus and a delivery port proximate the distal end of the sheath, wherein fluid from the fluid reservoir can be delivered through the delivery lumen to the delivery port using the fluid supply apparatus; and ablation apparatus including an electrode and an energy source operably connected to the electrode through a conductor, wherein the electrode is attached to the sheath proximate the distal end of the sheath and the conductor extends through the sheath to the electrode.

In some embodiments of systems according to the second aspect, the systems may include one or more of the following features: a return lumen in the sheath, wherein the return lumen includes a return port proximate the distal end of the sheath and a waste port proximate the proximal end of the sheath, wherein at least a portion of fluid delivered to an enclosed volume through the delivery port of the delivery lumen can be removed from the enclosed volume through the return lumen; an expansion device on an exterior surface of the sheath, wherein the expansion device has a delivery configuration in which the expansion device is unexpanded and an expanded configuration in which the expansion device is expanded to increase its size as compared to the delivery configuration; the energy source may be a direct current (DC) electrical source, a Radio Frequency (RF) energy source, an ultrasonic energy source, a microwave energy source, a vibration energy source, a laser, and/or a combination of any two or more thereof; a temperature sensing system including a temperature sensor located proximate the distal end of the sheath; a pump in the form of a peristaltic pump; etc.

In a third aspect, some embodiments of a method of impairing smooth muscle tissue function may include locating the sheath of any system described in the two preceding paragraphs within a body cavity; delivering fluid to the body cavity through the delivery lumen using the fluid supply apparatus, wherein the electrode of the ablation apparatus is located in the fluid delivered to the body cavity; delivering energy to the electrode from the energy source, wherein the energy is sufficient to impair functioning of at least a portion of smooth muscle tissue proximate a wall of the body cavity.

In a fourth aspect, some embodiments of a smooth muscle tissue impairment system as described herein may include an elongated sheath having a proximal and a distal end, wherein a longitudinal axis extends between the proximal end and the distal end; fluid supply apparatus including a fluid reservoir and a pump; a delivery lumen extending through the sheath, wherein the delivery lumen has an input port operably connected to the fluid supply apparatus and a delivery port proximate the distal end of the sheath, wherein fluid from the fluid reservoir can be delivered through the delivery lumen to the delivery port using the fluid supply apparatus; and ablation apparatus comprising: an ablation device extending through the sheath, wherein the ablation device can be moved distally and proximally relative to the sheath; an electrode attached to the ablation device proximate a distal end of the ablation device; and an energy source operably connected to the electrode through a conductor extending through the ablation device; wherein movement of the ablation device distally and proximally relative to the sheath moves the electrode distally and proximally relative to the sheath. The ablation apparatus may include a distal guide element located proximate a distal end of the ablation device, wherein the distal guide element includes an expandable device expandable from a compact configuration to an enlarged configuration; and the electrode may be movable along the ablation device between the distal end of the sheath and the distal guide element.

In some embodiments of systems according to the fourth aspect, the systems may include one or more of the following features: a return lumen in the sheath, wherein the return lumen includes a return port proximate the distal end of the sheath and a waste port proximate the proximal end of the sheath, wherein at least a portion of fluid delivered to an enclosed volume through the delivery port of the delivery lumen can be removed from the enclosed volume through the return lumen; an expansion device on an exterior surface of the sheath, wherein the expansion device has a delivery configuration in which the expansion device is unexpanded and an expanded configuration in which the expansion device is expanded to increase its size as compared to the delivery configuration; the energy source may be a direct current (DC) electrical source, a Radio Frequency (RF) energy source, an ultrasonic energy source, a microwave energy source, a vibration energy source, a laser, and/or a combination of any two or more thereof; a temperature sensing system including a temperature sensor located proximate the distal end of the sheath; a pump in the form of a peristaltic pump; etc.

In a fifth aspect, some embodiments of a method of impairing smooth muscle tissue function may include locating the sheath of the system within a body cavity; delivering fluid to the body cavity through the delivery lumen using the fluid supply apparatus, wherein the electrode of the ablation apparatus is located in the fluid delivered to the body cavity; delivering energy to the electrode from the energy source, wherein the energy is sufficient to impair functioning of at least a portion of smooth muscle tissue proximate a wall of the body cavity; moving the electrode within the body cavity after delivering energy to the electrode, followed by delivering additional energy to the electrode after the moving.

In a sixth aspect, some embodiments of a smooth muscle tissue impairment system as described herein may include a conformable body having an outer surface that includes a delivery configuration and an expanded configuration, wherein, in the expanded configuration the conformable body conforms to the shape of a space in which it is located; a vibration energy source operatively coupled to the outer surface of the conformable body, wherein the vibration energy source causes the outer surface of the conformable body to vibrate when the vibration energy source is activated.

In some embodiments of systems according to the sixth aspect, the systems may include one or more of the following features: the conformable body is a balloon; the conformable body is a sheath; the outer surface of the conformable body includes nitinol; the vibration energy source is an ultrasound energy source; etc.

In a seventh aspect, a method of impairing smooth muscle tissue function may be provided that includes locating the conformable body of any system described in the two preceding paragraphs within a body cavity; expanding the conformable body such that at least a portion of the conformable contacts and conforms to at least a portion of an interior wall of the body cavity; delivering vibration energy to the outer surface of the conformable body, wherein the vibration energy is sufficient to impair functioning of at least a portion of smooth muscle tissue proximate the wall of the body cavity.

In an eighth aspect, some embodiments of a smooth muscle tissue impairment system as described herein may include an expandable body having a plurality of independent chambers arranged along a longitudinal axis, wherein each independent chamber can be expanded independently of the other independent chambers in the expandable body, and wherein each independent chamber has a delivery configuration and an expanded configuration, wherein, in the expanded configuration the independent chamber expands to occupy a volume greater than a volume occupied by the independent chamber in the delivery configuration; and an expansion source selectively coupled to the plurality of independent chambers of the conformable body, wherein the expansion source can expand each independent chamber from the delivery configuration to the expanded configuration.

In some embodiments of systems according to the eighth aspect, the systems may include one or more of the following features: the plurality of independent chambers is a plurality of balloons; an ablation apparatus that includes an electrode and an energy source operably connected to the electrode through a conductor, wherein the electrode is attached to an outer surface of the conformable body.

In another aspect, a method of impairing smooth muscle tissue function may be provided that includes locating the expandable body of any system described in the two preceding paragraphs within a body cavity; selectively expanding one or more independent chambers of the plurality of independent chambers such that the expanded independent chambers apply pressure to at least a portion of a wall of the body cavity, wherein the pressure is sufficient to impair functioning of at least a portion of smooth muscle tissue proximate the wall of the body cavity after the expanded body is removed from the body cavity.

In another aspect, some embodiments of a bronchoscopy-based ablation device as described herein may include a fluid delivery apparatus (that includes a fluid delivery lumen that includes a fluid delivery proximal end and a fluid delivery distal end) and a fluid return apparatus (that includes a fluid return lumen that includes a fluid return proximal end and a fluid return distal end), a first electrode operatively connected to a conductor and an energy source, a second electrode operatively connected to the first electrode, wherein the second electrode is a virtual electrode comprising a conductive fluid, wherein the electrode is proximate the fluid delivery distal end; and wherein the device is configured to pass through a body cavity comprising a pulmonary lumen.

In another aspect, a method of ablating is provided wherein the method includes locating a first balloon within a pulmonary lumen defined by a pulmonary lumen wall; and causing the first balloon to apply pressure to the pulmonary lumen wall, wherein the pressure is sufficient to affect at least a portion of smooth muscle tissue proximate the pulmonary lumen wall.

In another aspect, a method of ablating is provided, wherein the method includes locating a distal end of a medical device within a pulmonary lumen and proximate smooth muscle tissue; wherein the medical device includes a bronchoscope, an occlusion balloon extending radially from the bronchoscope, an electrode located on either the occlusion balloon or the bronchoscope, a conductive fluid delivery lumen passing through the occlusion balloon and having an opening proximate the distal end of the medical device, and a conductive fluid return lumen passing through the occlusion balloon and having an opening proximate the distal end of the medical device; locating a virtual electrode proximate the distal end of the medical device; transferring energy to at least a portion of the virtual electrode, wherein the energy transferred is sufficient to affect at least a portion of the smooth muscle tissue; and cooling at least a portion of the surface of the occlusion balloon.

In another aspect, a method of ablating is provided, wherein the method includes locating a medical device within a pulmonary lumen, wherein the medical device has a longitudinal axis passing from a distal end to the proximal end of the medical device, wherein a distal portion of the medical device comprises a coating that comprises a dielectric material and faces outward from the longitudinal axis and toward a cell comprising an ionically active membrane;

and transferring energy to the dielectric coating, wherein the energy transferred is sufficient to affect the cell.

In another aspect, a method of ablating is provided, wherein the method includes locating an ultrasound energy source within a pulmonary lumen defined by a pulmonary lumen wall; and delivering ultrasound energy from the ultrasound energy source, wherein the ultrasound energy is sufficient to affect at least a portion of smooth muscle tissue proximate the pulmonary lumen wall.

In another aspect, a method of ablating is provided, the method including locating a vibration transfer article within a pulmonary lumen defined by a pulmonary lumen wall; and delivering vibration energy to the vibration transfer article, wherein the vibration energy is sufficient to affect at least a portion of smooth muscle tissue proximate the pulmonary lumen wall.

In another aspect, a method of ablating is provided, wherein the method includes locating a source of energy proximate a smooth muscle or a body lumen supplying blood to the smooth muscle; and delivering the energy to the body lumen; wherein the energy is sufficient to affect smooth muscle tissue or the body lumen.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an electrode may be used to refer to one, two, or more electrodes.

The term "and/or" means one or all of the listed elements or a combination of any two or more of the listed elements.

The above summary is not intended to describe each embodiment or every implementation of the ablation systems described herein and methods of using the same. Rather, a more complete understanding of the ablation systems and methods of using the same will become apparent and appreciated by reference to the following Description of Illustrative Embodiments and claims in view of the accompanying figures of the drawing.

BRIEF DESCRIPTION OF THE VIEWS OF THE DRAWING

FIG. 15A depicts a portion of another tissue ablation system located in a body cavity.

DESCRIPTION OF ILLUSTRATIVE EMBODIMENTS

Figure 1:
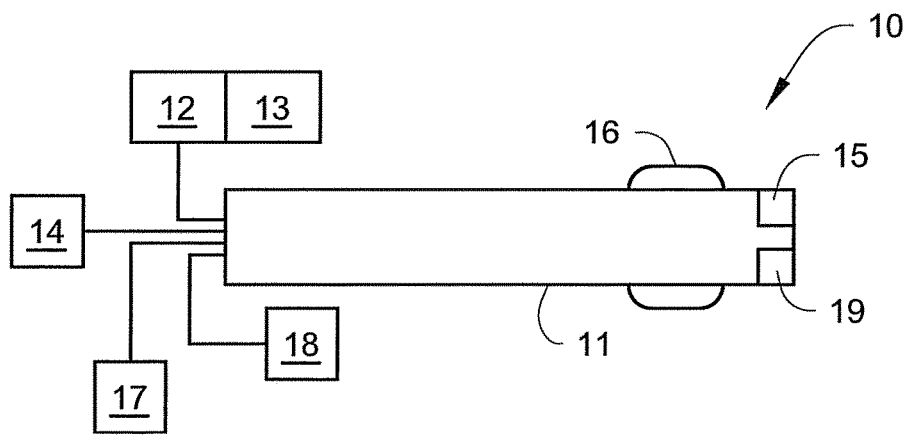
FIGS. 1-3 are schematic diagrams of three different smooth muscle tissue impairment systems described herein.

In the following description of illustrative embodiments, reference is made to the accompanying figures of the drawing which form a part hereof, and in which are shown, by way of illustration, specific embodiments of smooth muscle tissue impairment systems and methods. It is to be understood that other embodiments may be utilized and structural changes may be made without departing from the scope of the present invention.

Systems and/or methods are described herein which can impair (e.g., ablate) functioning of a smooth muscle layer lining a variety of body cavities (e.g., bronchi, blood vessels, etc.). Such smooth muscle tissue impairment may be useful in treating a variety of conditions resulting from unwanted spasms of the smooth tissue (e.g., asthma, etc.). It may be preferable to impair functioning of the smooth muscle tissue while reducing or avoiding damage to the endothelium covering such smooth muscle tissue within a body cavity, thereby potentially reducing or preventing strictures and/or scarring, and potentially reducing or preventing collateral damage. It may also be preferable that treatment be done quickly while affecting a relatively large amount of smooth musculature.

One or more embodiments of the systems and methods described herein may include the use of electrodes and fluid to allow treatment at a distance from an actual electrode site. The electrodes are used to supply energy which is then transferred from the electrodes through the fluid and to the tissue surrounding the fluid. In other words, in some embodiments the fluid serves as a virtual electrode that is intimate contact with the surrounding tissue.

Some embodiments of the present disclosure may include the use of multiple energy sources to generate ablative energy. In other embodiments, the electrode may be movable relative to other structures used to deliver the electrode and/or fluid. Since the smooth muscle itself does not line the body cavity, some embodiments of the systems and methods described herein may be designed to reduce endothelial damage; reduce local inflammation, strictures, or scarring; and reduce collateral damage while increasing impairment of at least a portion of a smooth muscle layer surrounding at least a portion of the body cavity.

FIG. 1 is a schematic diagram of one illustrative embodiment of a smooth muscle tissue impairment system. The system 10 includes a sheath 11, fluid supply apparatus including a reservoir 13 and pump 14. Fluid from the reservoir can be delivered through the sheath 11 using the pump 14. The pump 14 can be any device capable of causing fluid from the reservoir 13 to pass through a lumen in the sheath 11. Examples may include, but are not limited to, peristaltic pumps, piston pumps, diaphragm pumps, syringe pumps, pressurized bladders that force fluid out of the reservoir 13, etc.

The system 10 also includes an ablation apparatus in the form of an energy source 14 and an electrode 15. The energy source 14 may, in some embodiments, be capable of delivering more than one type of energy to an electrode 15 (or electrodes). For example, the energy source may be capable of delivering RF energy and/or DC energy to the same electrode(s). Although depicted as a single energy source 14, if multiple types of energy are to be delivered, the system may include multiple energy sources to deliver the different types of energy.

The electrode 15 may, in some embodiments, be movable within a body cavity in which it is deployed to allow for more widespread treatment of the smooth muscle tissue lining the walls of the body cavity. The electrode movement may be performed by moving the sheath and the electrode and/or by moving the electrode separately from the sheath or other positioning device.

The system 10 may also include an optional expansion device 16 that may be expanded from a delivery configuration to an expanded configuration using an expansion source 17 (if expansion device 16 is, e.g., a balloon, then expansion source 17 may be, e.g., a source of inflation fluid).

The system 10 may also include a temperature sensing system that includes, e.g., a temperature sensor 19 on the sheath 11 and temperature sensing device 18 connected to the sensor 19 through the sheath 11.

Figure 2:
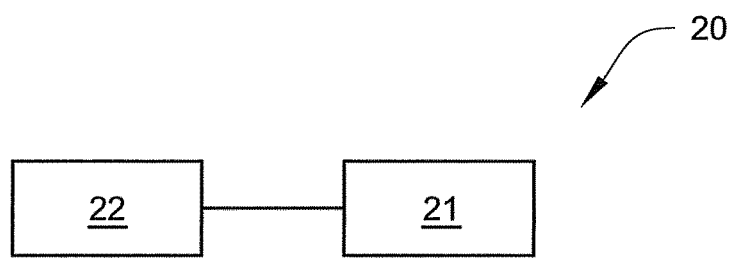
Figure 3:
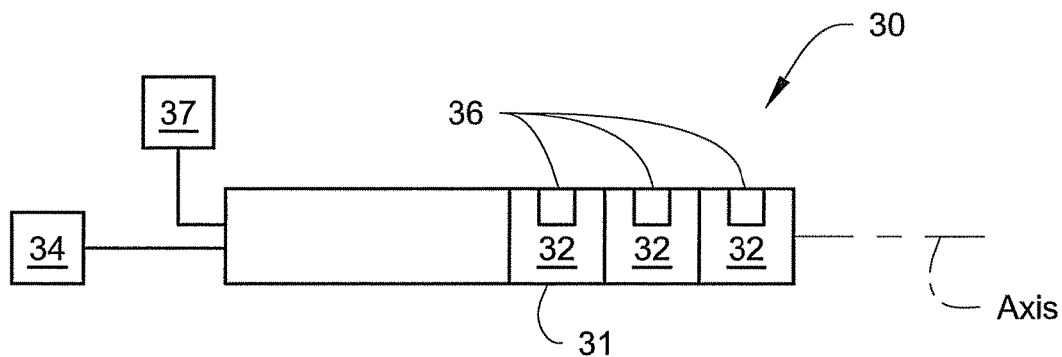

Another illustrative embodiment of a smooth muscle tissue impairment system is depicted in FIG. 2. The system 20 includes a conformable body 21 having an outer surface that has a delivery configuration and an expanded configuration, wherein, in the expanded configuration the conformable body conforms to the shape of a space in which it is located. The system 20 also includes a vibration energy source 22 connected to the conformable body 21. The vibration energy source 22 preferably causes the outer surface of the conformable body 21 to vibrate when the vibration energy source 22 is activated Still another illustrative embodiment of a smooth muscle tissue impairment system 30 is depicted in FIG. 3 and includes an expandable body 31 that includes a plurality of independent chambers 32 arranged along a longitudinal axis, wherein each independent chamber 32 can be expanded independently of the other independent chambers 32 in the expandable body 31, and wherein each independent chamber 31 has a delivery configuration and an expanded configuration, wherein, in the expanded configuration the independent chamber 32 expands to occupy a volume greater than a volume occupied by the independent chamber 32 in the delivery configuration. The system 30 also includes an expansion source 34 selectively coupled to the plurality of independent chambers 32 of the conformable body 31, wherein the expansion source 34 can expand each independent chamber 32 from the delivery configuration to the expanded configuration.

The system 30 also includes an optional ablation apparatus that includes one or more electrodes 36 and an energy source 37 operably connected to the electrodes, wherein the electrodes 36 are attached to an outer surface of the expandable body 31. In the depicted embodiment, each independent chamber 32 includes at least one (possibly more) electrodes 36 such that expansion of the chamber 32 and activation of the electrode 36 can be performed at the same time or different times.

Figure 4:
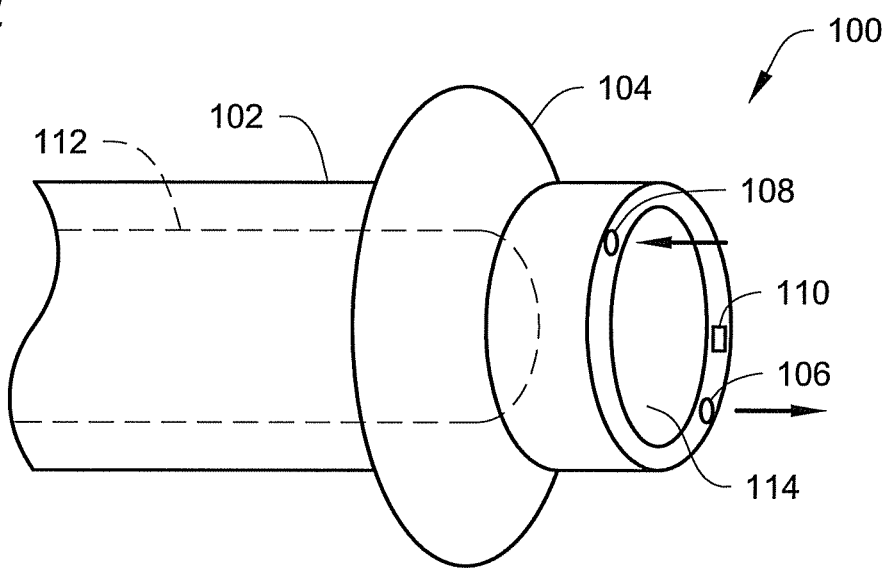
FIG. 4 depicts a portion of a system according to the present disclosure.

A portion of another system 100 is depicted in FIG. 4. As shown, the system 100 that includes a sheath 102 (e.g., an outer sheath, a detachable sheath, etc.) having an optional expansion device 104 (e.g., a balloon cuff, etc.) on the outside thereof; two lumens 106 and 108 passing through the sheath 102; and an electrode 110. In one or more embodiments, a bronchoscope 112 or other device may be located within the sheath.

In some embodiments, the sheath 102 may be a sheath that could be used in a variety of laparoscopic or endoscopic procedures. The sheath 102 includes a proximal end and a distal end opposite the proximal end and a major lumen 114 passing through the sheath 102, wherein the major lumen 114 has a major lumen opening proximate the distal end of the sheath 102.

In one or more embodiments, the sheath 102 may also include one or more additional lumens 106 and 108 passing through the sheath. The one or more additional lumens may include lumen openings or ports that are proximate the distal end of the sheath 102.

For example, in some embodiments, a sheath 102 may include a fluid delivery lumen 106 having an opening proximate the distal end of the sheath 102. In one or more embodiments, the sheath 102 may also include a fluid return lumen 108 having an opening proximate the distal end of the sheath. In some embodiments, the fluid delivery lumen 106 and/or the fluid return lumen 108 may pass through the wall of the sheath 102.

In some embodiments, a device 100 may include a fluid supply apparatus, that may include the fluid delivery lumen 106 and, optionally, a fluid return lumen 108. In some embodiments, the fluid supply apparatus may include a pump to cause a fluid to flow through the fluid delivery lumen 106 and/or fluid return lumen 108. In some embodiments, the system may include an apparatus capable of applying a negative pressure (e.g., a vacuuming apparatus, a suctioning apparatus, etc.) on the fluid return lumen in order to draw liquid from the distal end of the sheath 102 through the return lumen 108.

The fluids used in connection with the systems and methods described herein may include, but are not limited to, aqueous fluids, saline, isotonic saline, hypertonic saline, an oil-based fluid, a viscous fluid, combinations thereof, etc. In some embodiments, the fluid may include an electrically conductive fluid, suspension material, etc. Further, the fluids used may be changed during the procedure. For example, isotonic saline may be used in one portion of the ablation procedure, but in another case where, e.g., there is a thicker smooth muscle layer recognized, 3% saline may be used. Similarly, the fluid may be changed when the energy source or ablation using vibration or another mode of energy is being planned In some embodiments, a sheath 102 may include an electrode 110 attached to the sheath 102. The electrode 110 may, for example, be located proximate the distal end of the sheath 102. In some embodiments, the electrode 110 is operatively connected to a source of energy via, for example, a conductor (e.g., a wire, etc.). In some embodiments, for example, the electrode 110 at the tip of the sheath 102 (or, for example, a separate electrode placed in the center of or end of the fluid delivery lumen) may be in contact with the fluid delivered (e.g., saline). When the electrode 110 and fluid (e.g., a conductive fluid, saline, hypertonic saline, etc.) are in contact, that may allow, for example, radiofrequency energy to be emitted while causing the fluid to flow through the fluid delivery lumen 106 that may be in a sheath 102 (or catheter, etc.). In this arrangement, functional impairment of, e.g., bronchial smooth muscle tissue may be widespread through the second generation bronchi to the level of small airways.

In some embodiments, the fluid return lumen may be used to remove some of the fluid (e.g., saline) delivered through the delivery lumen to produce fluid circulation or an irrigation-like mechanism. Circulating fluid may not be needed, in some embodiments, if there is, for example, some movement of the fluid (e.g., saline) through some connecting bronchi to another low bar bronchial system. In one or more embodiments, circulating fluid may cool an endothelium and may thus prevent thermal injury to the endothelium while delivering energy.

In some embodiments, a system 100 may include an agent delivery lumen, which may pass though the sheath 102 (or catheter) may be used to inject one or more pharmaceutical agents that may dissolve in the fluid (e.g., saline) in case of, for example, paradoxic bronchospasm as a result of the fluid (e.g., saline) or the radiofrequency energy being delivered acutely. In some embodiments, the pharmaceutical agent may be a beta-2 agonist. In one or more embodiments, steroids may also be included with or added to the fluid (e.g., saline) with or without the bronchodilator. In some embodiments, other agents may also be used including, but not limited to, lidocaine or other topical anesthetics (e.g., cocaine, bupivicane, etc.).

Combination therapy with a pharmaceutical agent and different modes of energy delivery described herein may be used. Thus, DC energy, for example, may be emitted through a solution containing one or more pharmaceutical agents. The resulting electroporation, electrolysis, etc. that is obtained may potentially change the characteristics of the endothelial layer so as to allow better tissue penetration of the pharmaceutical agent to reach the smooth muscle to produce temporary or permanent effects (e.g., RF/DC energy facilitated pharmaceutical delivery).

A system as described herein may also include one or more temperature sensors. These temperature sensors may be placed within or through a lumen and/or in a sheath wall and may allow monitoring of radiofrequency or other energy delivery by detecting the temperature of fluid and/or tissue using the sensor.

The location and type of temperature sensing used in connection with the systems and methods described herein may vary in different embodiments. For example, multiple temperature sensors (e.g., thermocouples, thermistors and/or combinations thereof) may be placed either exposed to the circulating fluid (e.g., saline, etc.) in the wall of the balloon, conformable device or within the energy delivery electrode itself. The pattern of heating gradients can be used in addition to or in place of absolute temperature as part of a dynamic algorithm to titrate energy delivery by, e.g., anticipating temperatures at the endoluminal surface and the wall of the body cavity.

The temperature sensors may be delivered in a fixed location, e.g., on an expansion device or other element that is fixed during use, or they may be mounted for movement as discussed, e.g., in connection with the movable electrodes described herein.

In some embodiments, the type and/or location of temperature sensor used may be selected/switched based on, e.g., whether DC or radiofrequency energy is being emitted by the electrodes. Both the location and type (e.g., thermocouple vs. thermistor) may be switched differently on or off based on the type of energy delivery and for hybrid energy delivery options (e.g., combinations of two or more types of energy selected from, e.g., DC, RF, vibration, ultrasound, microwave, etc.).

A system as described herein may also include one or more position sensors that may be used to provide feedback to a user regarding the positions of one or more other components in the systems. For example, the position sensors may be used to provide position information with respect to the electrodes, a sheath, etc.

In some embodiments, a system as described herein may include one or more contrast lumens, which may pass through the sheath and may be used to inject a fluoroscopy-visible aerosolized contrast or other contrast to perform bronchograms. In one or more embodiments, the contrast (or hypertonic saline or other fluid) may be flushed out or retrieved (suctioned) by, for example, the one or more contrast lumens and/or the fluid return lumen.

In one or more embodiments, an electrode 110 used in connection with the systems and methods described herein may operate as an ablation electrode. For example, a source of energy may provide energy to the electrode 110, which may, in turn, provide energy to a material (e.g., biological tissue), resulting in ablation of a portion of the material.

In one or more embodiments of the systems and methods described herein, the tissue to be impaired or ablated may include smooth muscle tissue lining a body cavity or lumen (e.g., airway smooth muscle tissue, a blood vessel supplying smooth muscle tissue, etc.). In some embodiments, the material may be impaired or ablated even when not in direct contact with the electrode 110 (e.g., ablation electrode) when energy is transferred to the electrode 110 by transferring the energy through the fluid delivered through, e.g., the sheath.

In some embodiments, the sheath 102 may include an expansion device 104. An expansion device 104 may include a cuff (e.g., a balloon cuff, etc.) or other expandable structure that may be used to close off a passageway, cavity, etc. In some embodiments, an expansion device 104 may be expanded by providing a fluid (e.g. a gas or liquid) to the expansion device 104.

In some embodiments, an expansion device 104 may be configured to be expanded and seal a bronchus (e.g., a bronchiole, a first-, second-, third-, fourth-order bronchus, etc.). An expansion device 104 may be used to stabilize the positioning of the sheath 102 in a body cavity (e.g., a pulmonary lumen, bronchus, bronchiole, blood vessel, etc.), for example, over a bronchoscope (e.g., ultra-thin or conventional). In one or more embodiments, one expansion device 104 may be used. In some embodiments, more than one expansion device 104 may be used.

In some embodiments, a system 100 may include a bronchoscope 112 or other device. The bronchoscope 112 may be delivered through the sheath 102. In some embodiments, an ultra-thin or conventional bronchoscope may be delivered through the sheath 102.

Figure 5:
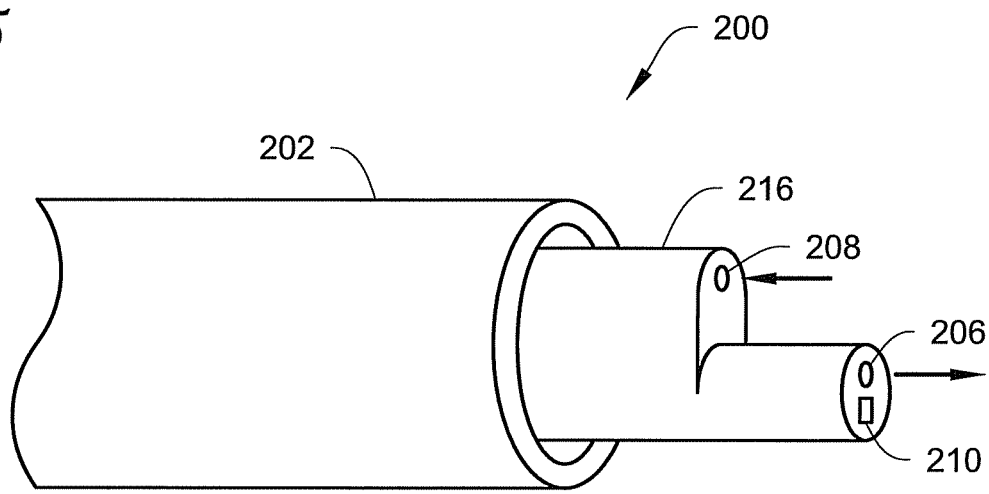
FIG. 5 depicts a portion of a system according to the present disclosure.

FIG. 5 depicts a portion of another illustrative system 200. The system shown in FIG. 5 may include a sheath 202 (e.g., an outer sheath) and a catheter 216 that includes an electrode 210, a fluid delivery lumen 206 with a fluid delivery lumen opening, and a fluid return lumen 208 with a return port opening proximate the distal end.

The sheath 202 depicted in FIG. 5 may be substantially similar to the sheath 102 depicted in FIG. 5 and described herein. In some embodiments, the sheath 202 may not include an electrode 210. In one or more embodiments, the sheath 202 may not include one or both of the fluid delivery lumen 206 or fluid return lumen 208. Although FIG. 5 does not depict an expansion device (e.g., occlusion balloon), an expansion device may be included to, for example, stabilize the sheath 202 within a body cavity (e.g., a bronchus, a bronchiole, etc.).

As depicted in FIG. 5, an electrode 210, a fluid delivery lumen 206, and fluid return lumen 208 may be provided by advancing a catheter 216 (or more than one catheter) that includes an electrode 210, fluid delivery lumen 206, and fluid return lumen 208 through the sheath 202. In one or more embodiments, the distal end of a catheter 216 may extend distally through the sheath distal end opening. In some embodiments, a catheter 216 may be advanced through the sheath 202 once the sheath 202 is in place (e.g., stabilized by an expansion device such as that shown in FIG. 4) and the bronchoscope 112 is removed from the sheath 202.

A potential feature of the system depicted in FIG. 5 may be the ability of the electrode 210 to move relative to the sheath 202 such that energy delivered by the electrode 210 can be moved throughout a body cavity in which the catheter 216 and the electrode 210 are deployed. As discussed herein, movement of the electrode(s) 210 can be used to impair/ablate smooth muscle tissue lining a larger portion of the walls of the body cavity.

In some embodiments, the electrode 210 may be located proximate a fluid delivery lumen opening. In some embodiments, the electrode 210 may be located proximate the fluid delivered through the fluid delivery lumen 206.

In some embodiments, the sheath 202 may include a bronchoscope therein, as shown in FIG. 4. The bronchoscope may be removed from the sheath 202, for example, to allow passage through the sheath 202 of a catheter 216, as shown in FIG. 5.

Figure 6:
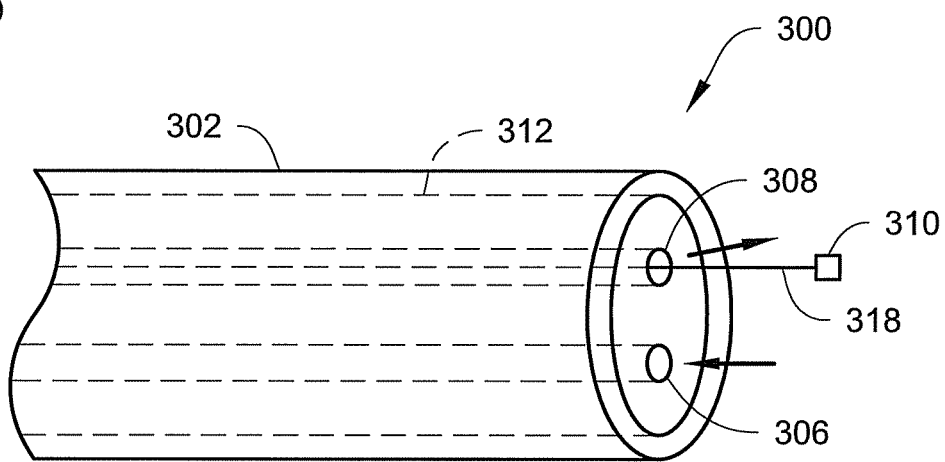
FIG. 6 depicts a portion of a system according to the present disclosure.

FIG. 6 depicts another illustrative embodiment of a system 300 that may be similar in some aspects to the system 100 as shown in FIG. 4. One difference may be that the fluid delivery lumen 306 and the fluid return lumen 308 are in the working channels of a bronchoscope 312, rather than being lumens within the wall of the sheath 102, as shown in FIG. 4. In other words, the bronchoscope itself may serve as a sheath. The device 300 depicted in FIG. 6 may alternatively include a sheath 302 through which the bronchoscope 312 passes, wherein the bronchoscope 312 may include, for example, one or more working channels.

The one or more working channels may include a fluid delivery lumen 306 for delivering a fluid through the bronchoscope 312 and exiting proximate a distal end of the bronchoscope 312. The one or more working channels of the bronchoscope 312 may also include a fluid return lumen 308 for retrieving a fluid from the distal end of the bronchoscope 312, wherein the fluid may flow proximally through the bronchoscope 312.

A bronchoscope 312, as shown in FIG. 6, may also include an electrode 310 that may pass through one of the one or more working channels of the bronchoscope 312. For example, an electrode 310 may be operatively connected to a conductor 318 (e.g., a wire, cable, etc.) that passes through one of the working channels of the bronchoscope 312 and may be operatively connected to an energy source.

A potential feature of the system depicted in FIG. 6 may be the ability of the electrode 310 to move relative to the sheath 302 and/or other components such that energy delivered by the electrode 310 can be moved throughout a body cavity in which the electrode 310 is deployed. As discussed herein, movement of the electrode(s) 310 can be used to impair/ablate smooth muscle tissue lining over a larger portion of the walls of the body cavity.

In one or more embodiments, the bronchoscope 312 may be located within a sheath 302 or catheter. In some embodiments, one or more of the working channels of the bronchoscope 312 may include a sheath or catheter.

In some embodiments, a bronchoscope 312 may be located within an outer sheath 302 in parallel with one or more catheters that may include an electrode 310, a fluid delivery lumen 306, a fluid return lumen 308, etc. Thus, in some embodiments, each of the fluid delivery lumen opening, fluid return lumen opening, and electrode 310 may be independently positioned relative to the others.

In one or more embodiments, the electrode 110, 210, and 310 may be fixed relative to the position of the sheath 102 (e.g., FIG. 4), may be independently positioned relative to the sheath 202 and fixed relative to one or both of the fluid delivery lumen opening and fluid return lumen opening (e.g., FIG. 5), or may be independently positioned relative to a bronchoscope 312 that includes a fluid delivery lumen 306 and/or a fluid return lumen 308 (e.g., FIG. 6).

Figure 7:
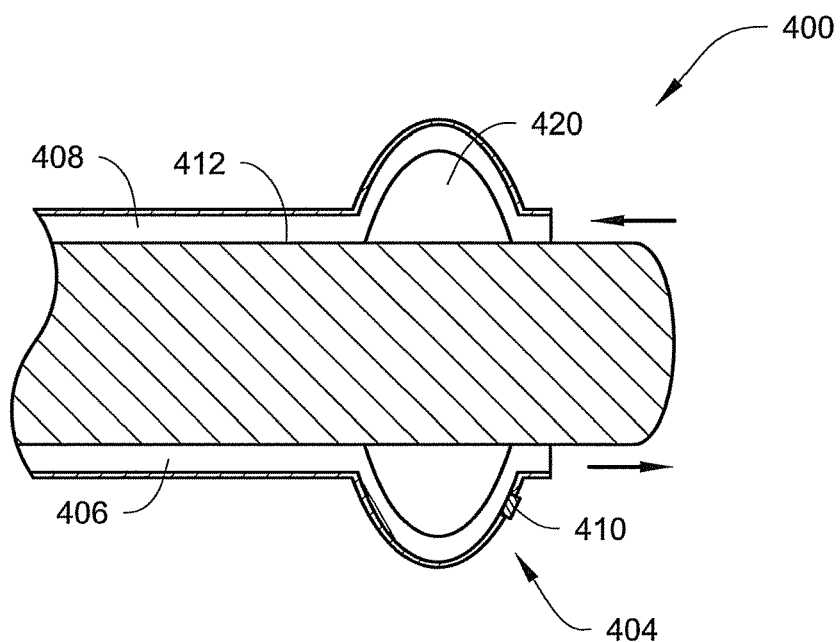
FIG. 7 depicts a portion of a system according to the present disclosure.

One or more embodiments of the systems described herein may include a device 400 that includes an expansion device 404 having an inflatable portion 420, a fluid delivery lumen 406 having a fluid delivery lumen opening, and fluid return lumen 408 having a fluid delivery lumen opening. As shown in FIG. 7, the inflatable portion 420 may extend outwardly from, for example, a bronchoscope 412. In some embodiments, the inflatable portion 420 may be inflated with a fluid (e.g., a gas and/or a liquid).

In some embodiments, the fluid delivery lumen 406 may pass through a fluid delivery portion of the surface of the expansion device 404. In some embodiments, the fluid return lumen 408 may pass through a fluid return portion of the surface of the expansion device 404. In some embodiments, substantially all of the surface of the expansion device 408 may include one or both of the fluid delivery path and the fluid return path. Although FIG. 7 shows that the fluid delivery path ("saline out") located opposite the fluid return path ("saline in"), some embodiments may include a plurality of fluid delivery paths and a plurality of fluid return paths alternating around the expansion device.

In some embodiments, the expansion device 404 may include an expansion device surface that includes a plurality of fluid containing layers wherein, for example, the fluid delivery lumen may pass through an outer layer of the surface of the 404 and the fluid return lumen may pass through a layer inside of the fluid containing layer that includes a fluid delivery lumen 406.

In some embodiments, an expansion device 404 may include an electrode 410. In some embodiments, the electrode 410 may be proximate a fluid delivery lumen opening. Electrode 410 may have any of the characteristics described herein regarding the electrodes depicted in FIGS. 4-6.

Figure 8:
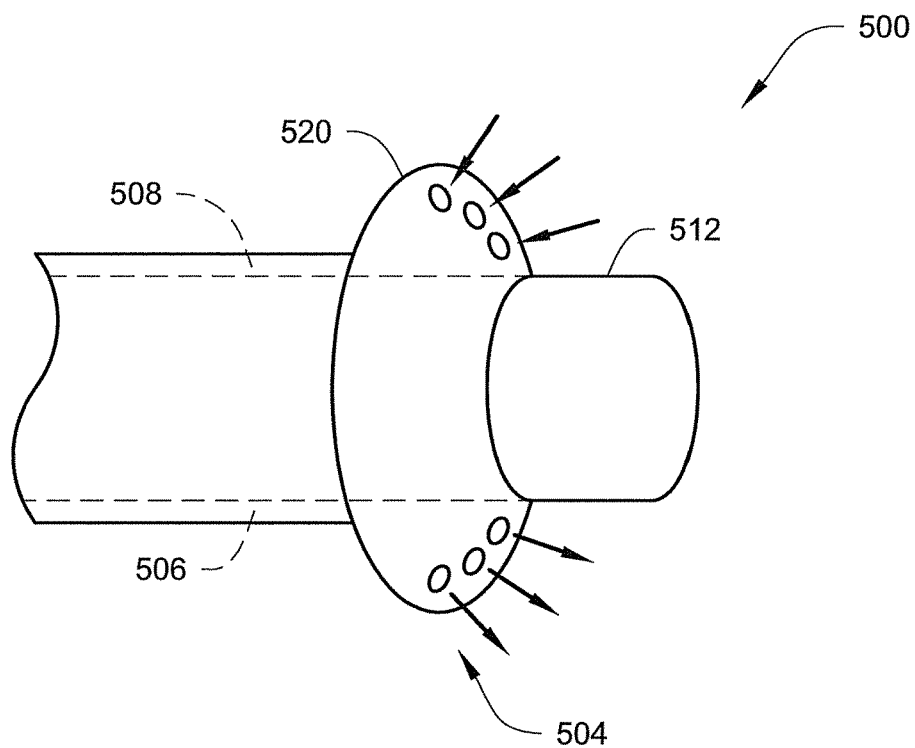
FIG. 8 depicts a portion of a system according to the present disclosure.

One or more embodiments of a device 500 according the present disclosure is shown in FIG. 8. In some embodiments, a fluid delivery lumen 506 may be in fluid communication with an inflatable portion 520 of the expansion device 504, as shown in FIG. 5. In one or more embodiments, the fluid delivery lumen 506 may also include a plurality of fluid delivery lumen openings. For example, an expansion device 504 may include a porous balloon portion, wherein a fluid may flow through the porous balloon portion.

In one or more embodiments shown in FIGS. 7 and 8, the expansion devices 404 and 504 may expand outwardly from the bronchoscope 412 and 512 toward a wall of a body cavity, thereby forming, for example, a stabilized position for the bronchoscope 412 and 512 (or sheath) in a body cavity or lumen. In FIGS. 4 and 5, the bronchoscope 412 and 512 may, in some embodiments, be removable.

Figure 9:
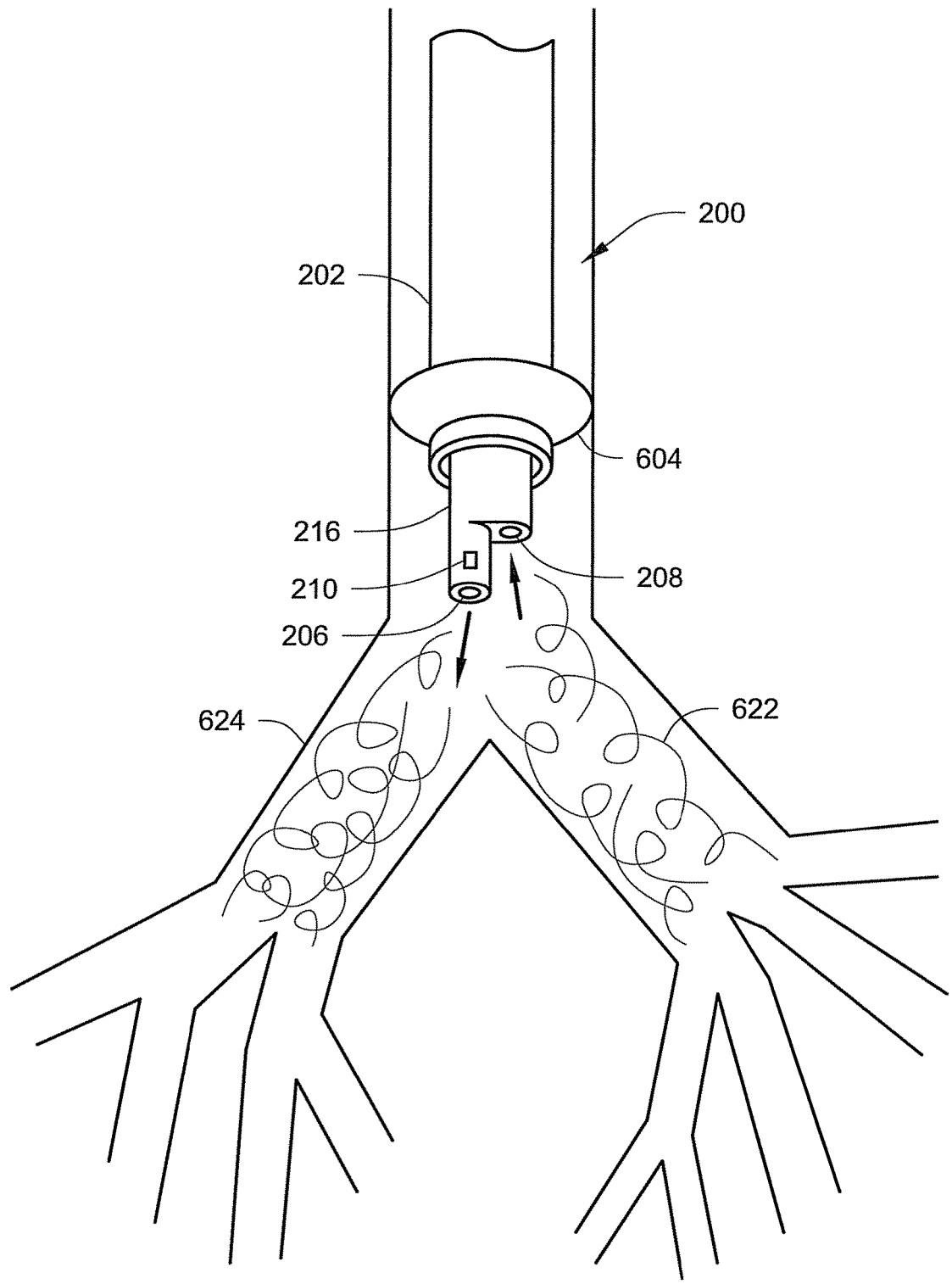
FIG. 9 depicts a portion of a system according to the present disclosure wherein the system is located within a body cavity.

FIG. 9 shows the device 200 of FIG. 9 located within a body cavity (e.g., a bronchus, bronchiole, etc.). The device 200 in FIG. 9 includes a sheath 200, an expansion device 604, and a catheter 216 that includes an electrode 210, a fluid delivery lumen 206, and a fluid return lumen 208.

FIG. 9 shows a quantity of a fluid 622 (e.g., a conductive fluid) flowing from the fluid delivery lumen opening and into one or more body cavities 624. In some embodiments, the fluid 622 may fill or may partially fill one or more body cavities 624 (e.g., one or more branched body cavities, bronchi, bronchioles, etc.).

In one or more embodiments, energy may be transferred to the electrode 210 which may transfer energy to the fluid 622 (e.g., conductive fluid). In some embodiments, the fluid 622 may be removed through the fluid return lumen 208.

As discussed elsewhere herein, a potential feature of the system depicted in FIG. 9 may be the ability of the electrode 210 to move relative to the sheath 202 such that energy delivered by the electrode 210 can be moved throughout a body cavity 624 in which the catheter 216 and the electrode 210 are deployed. As discussed herein, movement of the electrode(s) 210 can be used to impair/ablate smooth muscle tissue lining over a larger portion of the walls of the body cavity as compared to a system in which the electrode is stationary.

Figure 10:
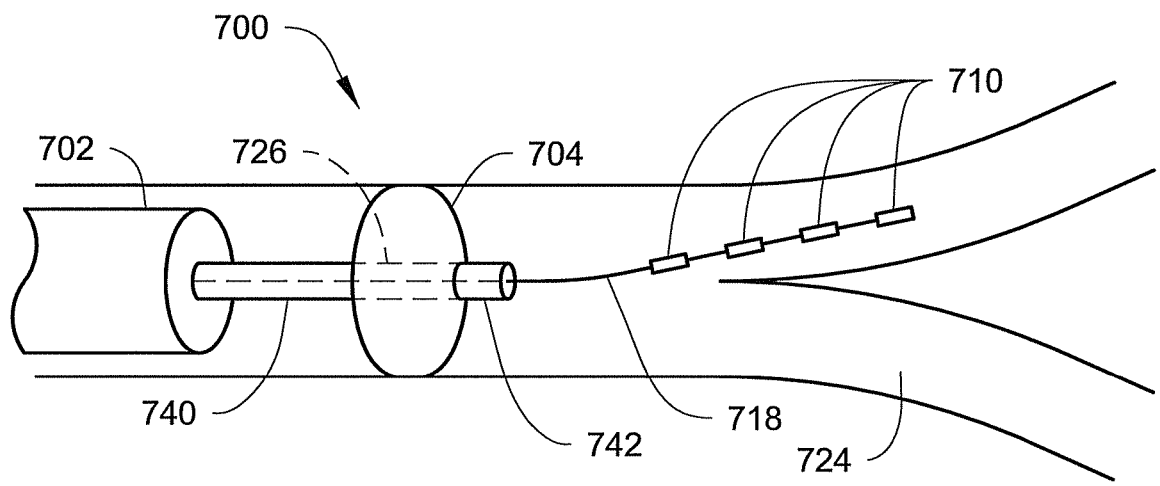
FIG. 10 depicts a portion of a system according to the present disclosure wherein the device is located within a body cavity.

FIG. 10 depicts another embodiment of a device 700 according to the present disclosure, wherein the device 700 includes an expansion device 704 (e.g., a movable expansion device) that includes an expansion device lumen 726 and that may or may not be operatively connected to a sheath or catheter 740 that can be advanced through the lumen 726 (or in some embodiments is fixedly attached to the expansion device 704 within the lumen 726).

The device 700 of FIG. 10 also includes a conductor 718 (e.g., a wire, cable, etc.) operatively connected to electrodes 710. The conductor 718 may preferably be delivered through a lumen in the catheter 740. Although multiple electrodes 710 are provided in the depicted embodiment, in some embodiments, the conductor 718 may be connected to only one electrode 710.

The electrodes 710 shown in FIG. 10 are moveable within a body cavity 724 by, e.g., advancing or retracting the conductor 718 and/or catheter 740. For example, the conductor 718 and attached electrodes 710 may be advanced through the expansion device lumen 726 until they enter the body cavity 724. Once deployed in the body cavity 724, the electrodes 710 may be moved in a variety of directions, e.g. distally, proximally, etc. to deliver energy to the smooth muscle tissue as desired. For example, as discussed herein movement of the electrodes can be used to impair/ablate smooth muscle tissue lining a larger portion of the walls of the body cavity.

In some embodiments, the electrodes 710 each may be operatively connected to a different conductive element within conductor 718 that may be insulated from and moved independently of other conductive elements in the conductor 718 to provide even more control over the energy delivery to the walls of the body cavity 724.

In yet another variation, the different electrodes may be separately and independently actuatable, in other words, the operator may be able to deliver energy through one (or more) of the electrodes 710 as desired. The electrodes 710 may, for example, be used to deliver energy in a sequential manner, with the electrodes 710 being successively used to deliver energy over a larger portion of the walls of the body cavity 724.

In some embodiments, the catheter 740 depicted in FIG. 10 may also include an optional electrode 742 that can be used alone and/or in combination with the electrodes 710 on the conductor 718.

In some embodiments, the catheter 740 may also include one or more lumens to deliver and/or remove fluids delivered to the area in which the electrodes are located.

In some embodiments, the catheter 740, expansion device 704 and related components may be delivered through a bronchoscope or other delivery device 702 (e.g., a sheath, etc.).

In one or more embodiments of the present disclosure, a system may include more than one energy source and may apply more than one energy source. For example, low level direct current with low fluid flow rates may be used in alternating fashion with higher fluid flow rates and radio frequency energy. In some embodiments, the same electrodes could be used for both radio frequency and direct current ablation or, alternatively, separate electrodes may be used.

For example, the electrode(s) may be movable along a column of fluid, as shown in FIG. 10. In areas with very little smooth muscle relative to endothelium, for example, direct current ablation may be used. In areas with relatively more smooth muscle as compared to endothelium, radio frequency energy may be delivered. The switching between two different sources of energy (or differing levels of the same type of energy) may be done manually (e.g. visually) or may be automated, for example, by measuring impedance changes as a result of the amount of smooth muscle, temperature changes at the surface of the tissue (e.g., bronchus), etc.

In one or more embodiments, a system may include a chiller to cool the fluid and may be adapted to deliver cool fluid as a form of cryoablation. In some applications (e.g., cardiac applications), cryoablation may be a type of energy that may spare an endothelium when used to ablate material in cardiac applications. In some embodiments, a surface of an expansion device (e.g., a balloon surface) may be cooled while extruding a fluid (e.g., saline) through which energy is delivered to tissue contact by the fluid.

In one or more embodiments, ion-channel or membrane-potential toxins could be used to preferentially affect smooth muscle while sparing the endothelium and may be an alternative to energy-based ablation or may be used in conjunction therewith. In some embodiments, Ganglion blocking agents and/or smooth muscle antagonists may be used in combination with direct current ablation. Substances that could be used, but may or may not require specific adjuvants to prevent significant systemic absorption may include but are not limited to: hexamethonium, suxanile choline, formaldehyde, formaldehyde derivatives, glycopyrrolate, trimethaphan, edrophonium, curare-like agents, dantrolene etc. Several other substances both within and without the general pharmacological family represented by these agents can be used. These agents may act as direct modifiers of the autonomic system or as a test to locate the exact spatial presence of the targeted autonomic fibers.

In one or more embodiments, a conformable body may be used to affect the smooth muscle tissues. For example, a conformable body may be located within a body cavity (e.g., bronchial airways, etc.) where the pressure exerted by the outer surface of the body against a wall of a body cavity may gradually be increased. The gradual increase in pressure may reduce and/or prevent sloughing of the endothelium and may compress the walls, which may contain fluid and/or arteries that supply smooth muscle tissue. While not wishing to be bound by theory, it is believed that the increased pressure may be sufficient to injure at least a portion of the smooth muscle tissue such that smooth muscle hyperreactivity may be affected (e.g., reduced).

In some embodiments, the systems may include an expandable body that includes multiple independent chambers in the form of, e.g., a multi-lumen long conformable balloon. For example, a guidewire may be advanced to a target location within a body cavity and the expandable body may be threaded over the wire. The body may be sufficiently long and may allow varying the location and degree of compression (e.g., sequentially) by using independent chambers to selectively treat different portions of the body cavity segment, which may, for example, be used to reduce bronchial airway hyperreactivity.

In some embodiments, thermal ablation electrodes may be provided in connection with the expandable body to optionally allow thermal ablation in conjunction with physical pressure. Because ischemic tissue typically dies earlier for a given temperature than non-ischemic tissue, the combination of thermal ablation and pressure may be useful and more vascular structures (e.g., smooth muscle) may be affected by this combination. In other words, the tissue may be ablated at temperatures lower than what would be typically expected for that temperature or power delivery when delivered in combination with physical pressure. By the use of concomitant pressure and/or vibration, etc., a more temperature sensitive environment may be created, thus allowing ablation of the smooth muscle with a lower risk of temperature mediated damage to the endothelium.

A wide variety of materials may be utilized to construct sheaths that may be used in connection with the systems and methods described herein. For example, the construction materials in a sheath may include, but are not limited to silicone, polyurethane, polyethylene, or any other suitable flexible material. Alternatively, in some embodiments, the construction materials to make a sheath may include a shape metal alloy, such as nitinol, or may include nitinol reinforcement. In one or more embodiments, the sheath may optionally be coated with a polymer or other material to ease passage into a body cavity (e.g., a bronchus, bronchiole, etc.). The sheath may include ablation electrodes, irrigation ports (e.g., fluid delivery lumen openings and/or fluid return lumen openings), and/or sensors (e.g. temperature, pressure, flow). In some embodiments, sheath electrodes may be long, linear electrodes useful to apply direct current energy along sites more proximal to the virtual electrodes.

In one or more embodiments, the systems and methods described herein may involve the use of multiple (e.g., two, three, etc.) layers. For example, a regular sheath may faun an outer layer, an expandable sheath (constructed of, e.g., nitinol) may form a middle layer, and through the lumen of the expandable sheath, a smaller tube may be placed. Once placed, a bronchoscope may be removed along with, for example, the outer sheath, which may allow the expandable sheath (e.g., a conformable nitinol sheath) to conform to the geometry of the body cavity or lumen (e.g., bronchial airways).

In some embodiments, the sheath(s) may be split. The sheath may be split and may be reinforced with, e.g., nitinol. The split end of the sheath may be placed over, for example, a smaller profile bronchoscope (which may have already been advanced to a target location) and may be advanced until the split end of the sheath reaches the end of the bronchoscope. In some embodiments, the sheath may optionally be kept in place at the target location via one or more expansion devices (e.g., a distal balloon cuff (or multiple balloons placed along the length of the sheath, or other mechanism)), the bronchoscope may be removed, and the liquid (e.g., saline) may be delivered through a sheath lumen or a catheter passed through the sheath. Alternatively, the fluid (e.g., saline) may flow through a lumen in a balloon (as shown in FIG. 7) or may pass through a porous balloon (as shown in FIG. 8).

Figure 11:
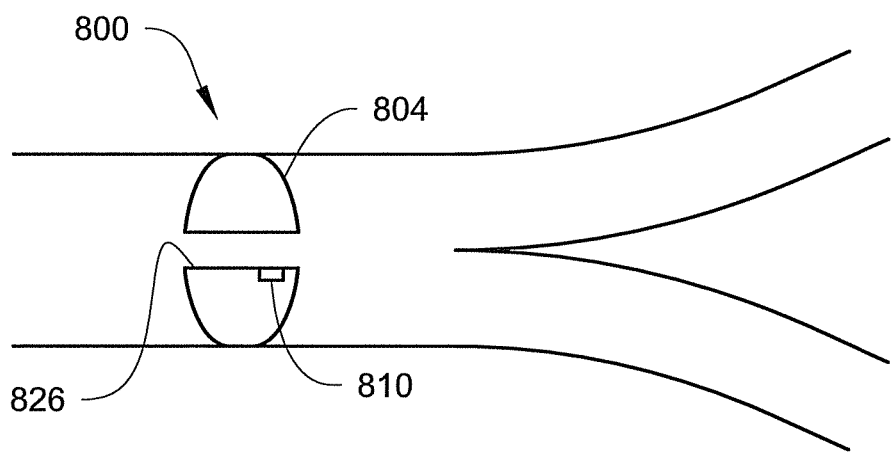
FIG. 11 depicts a portion of a system according to the present disclosure wherein the system is located within a body cavity.

FIG. 11 depicts another embodiment of a system 800, wherein the system 800 includes an expansion device 804 (e.g., a moveable expansion device) that may include a lumen 826 and an electrode 810 and may or may not be operatively connected to a sheath or catheter.

In one or more embodiments, the delivery of a fluid through the fluid delivery lumen and removal of the fluid through the fluid return lumen may result in a circulation of fluid within a body cavity or lumen. In some embodiments, a fluid cooler (e.g., a chiller) may be provided in which fluid may be cooled prior to delivery through the fluid delivery lumen. In some embodiments, delivery of a fluid at a temperature lower than 37° C. may be useful.

In another embodiment, a deflectable catheter (e.g. a standard electrophysiology catheter) could be placed in a lumen of the sheath to aid in navigation and steering. The deflecting catheter can go through the central lumen or could go through an eccentric monorail-type lumen on the sheath.

In another embodiment, the electrode used to deliver energy as described herein and/or sensors can be "floating" or moveable through the body cavity along a column of fluid. Saline (or other fluid) can be used to fill the distal airway branches and a sliding column electrode can be advanced and retracted to deliver energy at multiple locations along the path of the electrodes. Thus a virtual electrode can be provided that can be used to affecting a large area. Moving the electrode(s) may allow adjustment in the intensity and/or duration of energy delivery to selected portions of a wall lining the body cavity. Moving the electrode(s) may also allow for delivery of different types of energy to selected portions of a wall lining the body cavity.

A track may be provided and could be used for advancing and retracting the sliding column sensors and electrodes. The track may be positioned in the center of the cavity or off-center. In particular, a track or monorail system could potentially be useful for floating an ultrasound probe used for either ablation or monitoring in a solution that will accentuate the focusing properties of ultrasound (e.g. graded impedance, forced impedance match) and for electrodes that move or float in a column of conductive fluid.

While the proximal end of the track may be held in position by a sheath, expansion device, etc. that is also used to deliver fluid and the electrodes, a distal guide element may also be provided to hold the distal end of a track in position. The distal guide element may also be an expandable device similar to those described herein.

Figure 12:
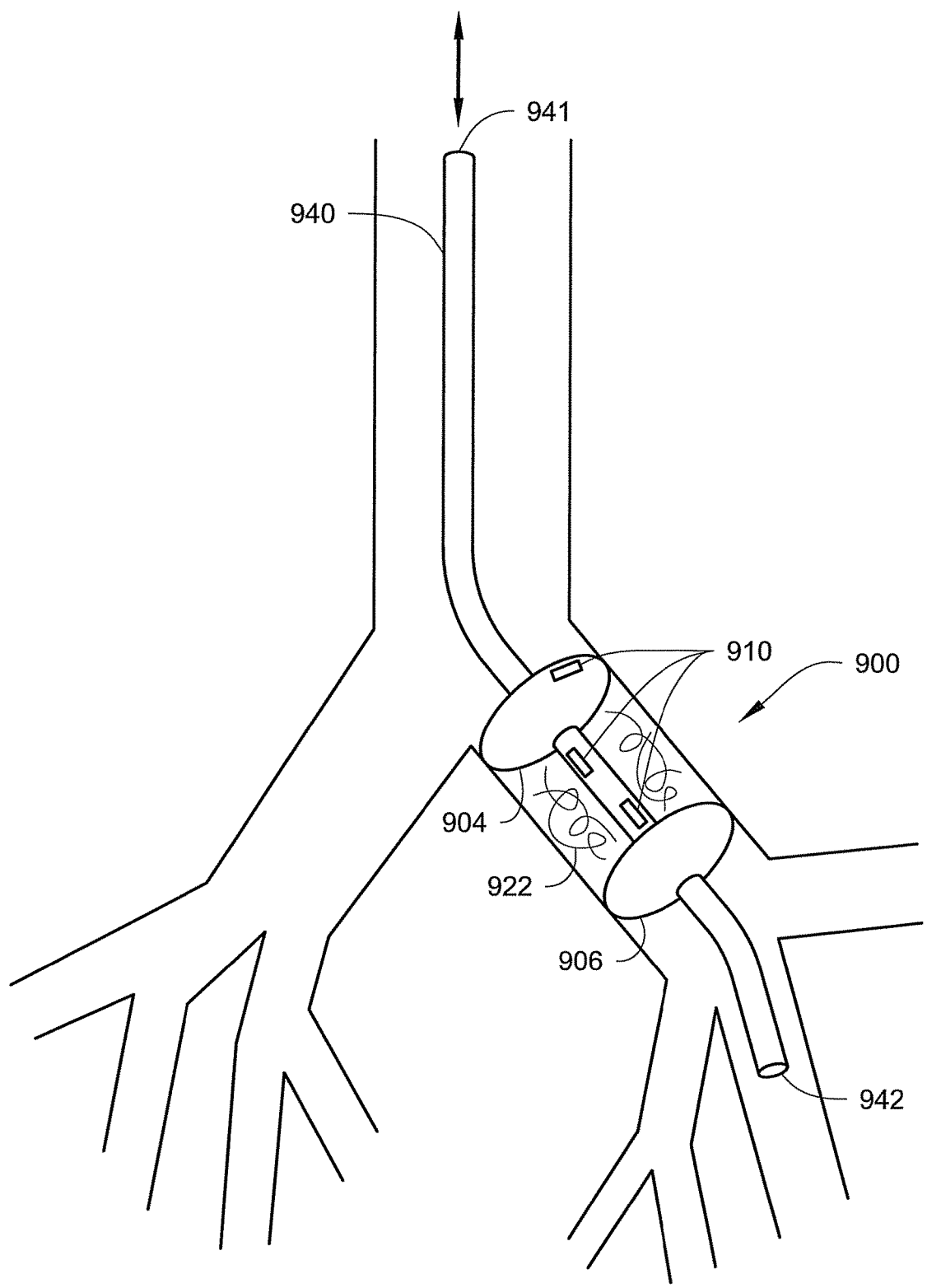
FIG. 12 depicts a portion of another system according to the present disclosure wherein the system is located within a body cavity.

Other potential embodiments of systems as described herein may be discussed with respect to FIG. 12 which depicts a system 900 placed in a body cavity. The system 900 includes a first expansion device 904 and a second expansion device 906. Although two expansion devices are depicted, the system may include only one or the other expansion device depending on the desired tissue to be treated, etc. Although not depicted, various other sensors may be provided to provide temperature sensing, navigation, etc. as discussed herein.

Also depicted in connection with FIG. 12 are electrodes 910 that may be used to deliver various modes of energy as discussed herein. The electrodes may be mounted for movement within the body cavity or they may be fixed to other components of the system. For example, one or more electrodes 910 may be provided on the expansion device 904 (e.g., etched on a balloon), etc.

Another feature depicted in connection with the system of FIG. 12 is the inclusion of a bypass lumen that will allow fluids to pass through the one or more expansion devices 904 and 906. For example, if the system 900 is used in a bronchial cavity, the bypass lumen 940 may allow air to pass between a proximal end 941 and a distal end 942 with or without mechanical facilitation. Use of the system 900 in other body cavities may result in passage of other fluids through the bypass lumen, e.g., blood, urine, gastric juices, etc.

The use of two expansion devices 904 and 906 as depicted in system 900 may allow for isolation of a internal volume between the device 904 and 906 that can be treated as discussed herein. Further, in some embodiments, the systems described herein may be used not only for ablation, but may be used to provide chemotherapeutic, antibronchospasmodic therapy by providing the ability to increase tissue contact time. Several alkaloids, as well as, e.g., smooth muscle relaxants, may be unsuitable for systemic delivery. Although the use of inhalants to deliver these therapies may be useful, the contact time of the tissue is relatively brief. Using the systems describe herein, however, may allow for increased contact time between such therapeutic agents and tissue and can, in some instances, result in the ablation of, e.g., bronchial smooth muscle tissue (which may be helpful for, e.g., severe asthmatics, etc.).

Figure 13:
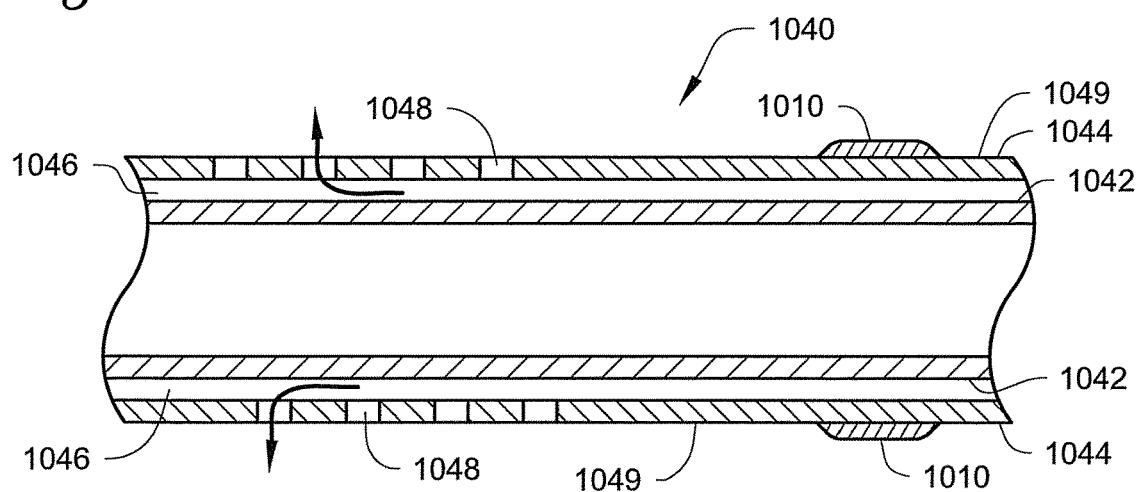
FIG. 13 is an enlarged cross-sectional view of a portion of another embodiment of a device that may be used in connection with the systems described herein.

Another embodiment of various features that may be used in connection with the systems described herein is depicted in FIG. 13, which is an enlarged cross-sectional view of a catheter or other elongated body 1040 that includes an inner tube 1042 and an outer tube 1044. This structure may be used in combination with many of the other fluid delivery bodies described herein where, e.g., the fluid to be delivered is preferably delivered in a direction transverse to the longitudinal axis of a delivery device.

The inner tube 1042 and outer tube 1044 preferably define a volume 1046 located between the outer surface of the inner tube 1042 and the inner surface of the outer tube 1044. Fluids may be delivered through the volume 1046 and exit the outer tube 1044 through openings 1048 provided in the outer tube 1044. The fluid delivered through the openings 1048 may be delivered under pressure.

The body 1040 may also include one or more electrodes 1010 such that the fluid delivered through the openings 1048 can serve as a pathway for the delivery of energy to the surrounding tissue. The electrodes 1010 may be located on the outer surface 1049 of the outer tube 1044 and/or they may alternatively be located between the inner tube 1042 and the outer tube 1044.

In some embodiments, the volume 1046 would be closed at the distal ends of the tubes 1042 and 1044. In other embodiments, the volume 1046 may be open at the distal ends of the tubes 1042 and 1044, but the space between the tubes may be sufficiently small such that a majority of the fluid delivered through the volume 1046 would exit through the openings 1048 before reaching the distal ends of the tubes 1042 and 1044.

Figure 14:
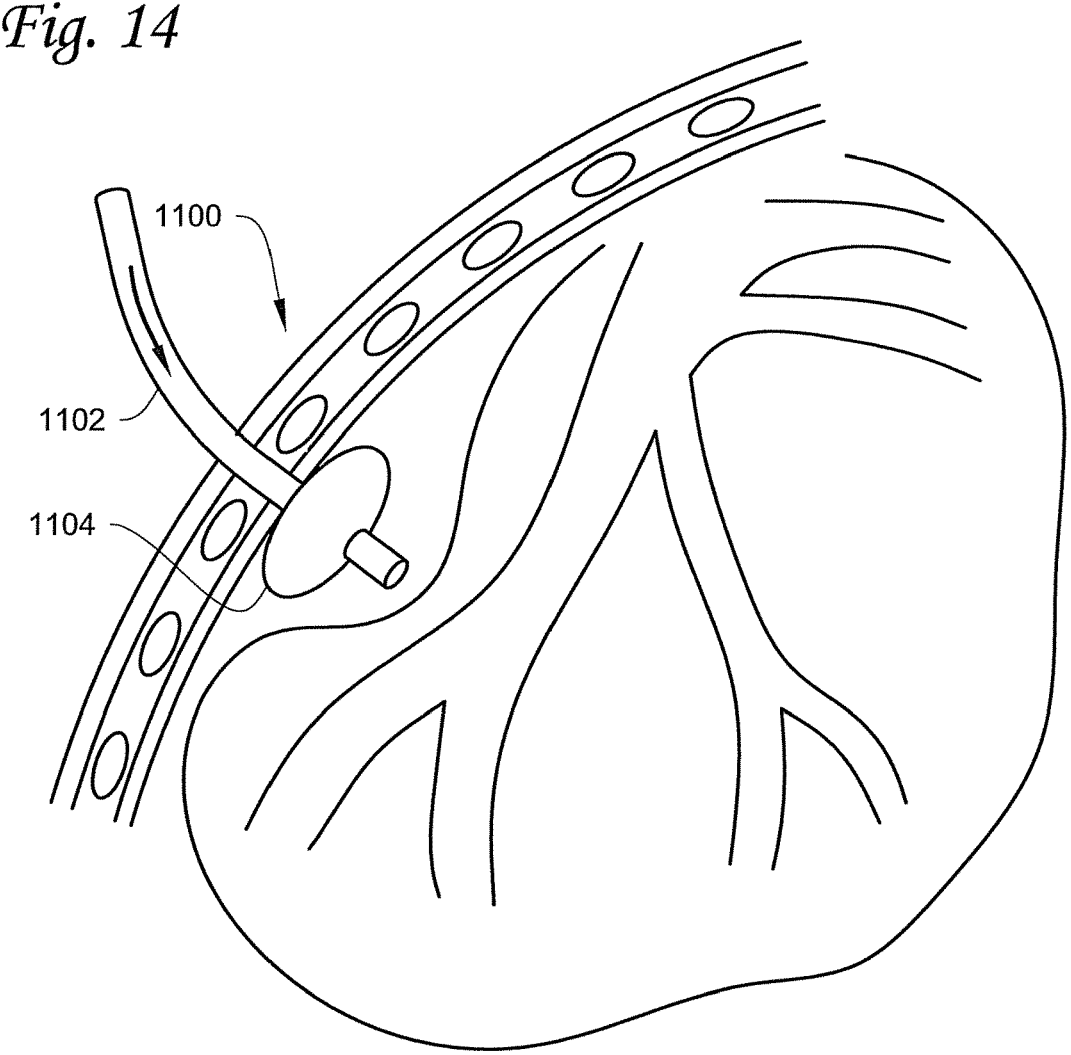
FIG. 14 depicts another device in use in a method that may be used to deliver energy into the pleural space.

Still another embodiment of a system is depicted in FIG. 14. The system 1100 includes a elongated body 1102 in the form of, e.g., a sheath that can potentially be introduced into the pleural space and used to introduce fluid therein for the delivery of ablation energy to the tissue surfaces defining the pleural space as described herein with respect to other body cavities. Although this approach may result in some superficial pulmonary ablation, the approach may be used to ablate the autonomics around the bronchi which may be useful for addressing bronchospastic disease.

Although not wishing to be bound by theory, it is possible that the autonomic innervation of the smooth muscles may be both epibronchial and endobronchial. Ablation giving direct current energy delivery, as well as electrolytic ablation using several of the iterations described could specifically cause neural lysis or ablation of the nerve endings or nerve trunks without necessarily causing smooth muscle ablation. Energy delivery targeting the autonomics may also cause significant autonomic modulation sufficient to minimize the likelihood of bronchospasm.

The elongated body 1102 may be, e.g., delivered intercostally and, optionally, include an expansion device 1104 to assist in retaining fluid in the pleural space and/or to hold the elongated body 1102 in place. Fluid may be delivered through the system using any of the various fluid delivery structures described herein (e.g., through the distal end of a lumen, a porous balloon, openings on the side of tube, etc.) Likewise, energy to be delivered through the fluid may be delivered to the fluid through an electrode placed in any of the many different locations described herein.

Figure 15B:
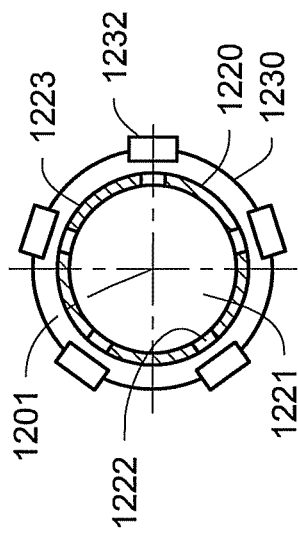
FIG. 15B is a cross-sectional view of the system of FIG. 15A taken along line 15B-15B in FIG. 15A.
Figure 15C:
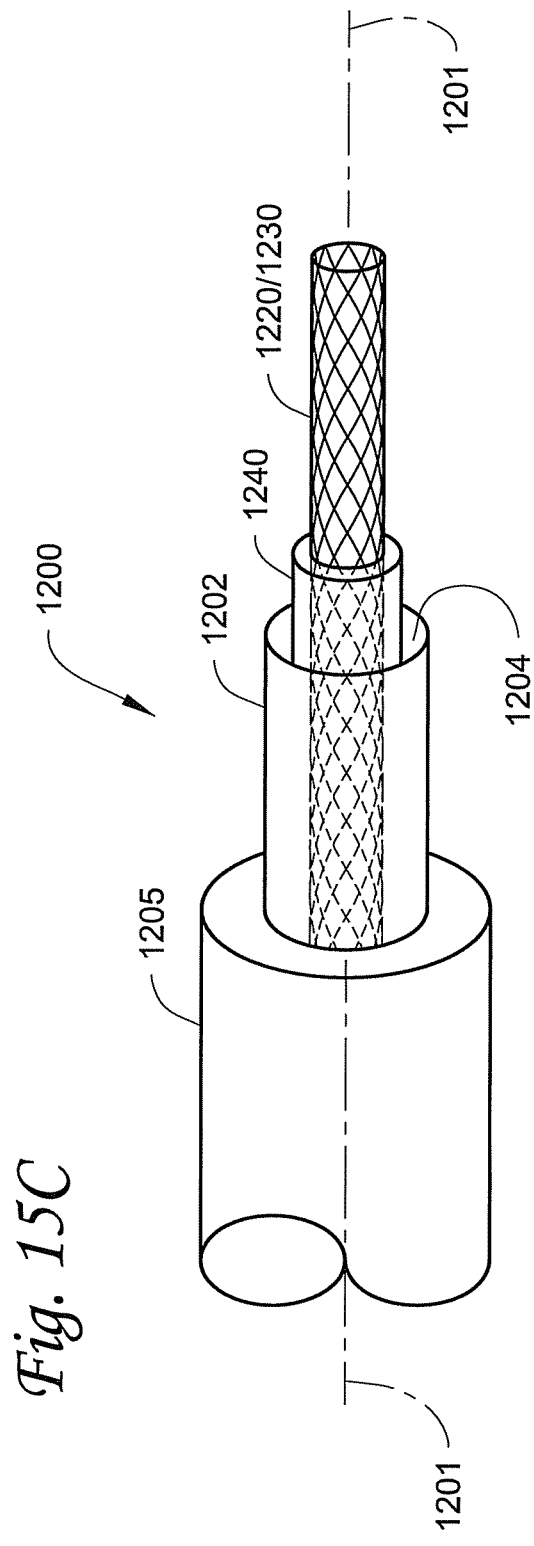
FIG. 15C is a partial cross-sectional view of the system of FIG. 15A before deployment of the ablation apparatus.

Yet another illustrative embodiment of a smooth muscle tissue impairment system is depicted in connection with FIGS. 15A-15C. The system 1200 preferably includes an elongated sheath 1202 that has a proximal end (not shown) and a distal end 1203. A longitudinal axis 1201 extends between the proximal end and the distal end 1203 along the length of the sheath 1202.

Although not depicted in FIGS. 15A-15C, the system 1200 may also preferably include fluid supply apparatus comprising a fluid reservoir and a pump. These components are, however, optional in some systems because they may be re-used with different sheaths and related components described as a part of the system 1200.

The system also includes a fluid delivery lumen 1242 extending through the sheath 1202, wherein the fluid delivery lumen 1242 has an input port (not shown) operably connected to the fluid supply apparatus (not shown) and a delivery port 1243 proximate the distal end 1203 of the sheath 1202. Fluid from the fluid reservoir of the fluid supply apparatus can be delivered through the fluid delivery lumen 1242 to the delivery port 1243 using the fluid supply apparatus. In some embodiments, the fluid delivery lumen 1242 may be formed directly in the sheath 1202, while in other embodiments, the fluid delivery lumen 1242 may be provided in a separate component, e.g., a catheter 1240 as depicted in FIG. 15A as described herein.

The system 1200 also preferably includes ablation apparatus 1210 that includes a fluid delivery element 1220 in fluid communication with the delivery port 1243 of the fluid delivery lumen 1242, the fluid delivery element 1220 defining a fluid volume 1221 (see, e.g., FIG. 15B). The fluid delivery element 1220 is preferably permeable to a fluid delivered into the fluid delivery element 1220 through the fluid delivery lumen 1242 such that the fluid can exit the fluid volume 1221 through the permeable fluid delivery element 1220. The fluid delivery element 1220 can preferably be moved distally and proximally relative to the longitudinal axis 1201 extending through the sheath 1202.

In some embodiments, the fluid delivery element 1220 may be provided in the form of a bladder that is permeable through a plurality of openings 1222 formed through a wall 1223 of the bladder (see, e.g., FIGS. 15A and 15B). The wall 1223 itself may or may not be permeable to the fluid. The term bladder as used herein may, in some embodiments, include flexible balloon-like structures that can expand due to the introduction of a pressurized fluid, as well as lumens that may or may not expand due to the introduction of a pressurized fluid.

The ablation apparatus of the system 1200 also preferably includes an ablation device 1230 positioned over at least a portion of the fluid delivery element 1220, wherein the ablation device 1230 is expandable radially relative to the longitudinal axis 1201. The ablation device 1230 can also preferably be moved distally relative to the longitudinal axis 1201 such that it can be advanced out of the distal end 1203 of the sheath 1202 (see, e.g., FIG. 15A as compared to FIG. 15C). The ablation device 1230 may, in some embodiments, be provided in the form of an expandable cage or other structure carrying electrodes 1232. Although described separately in this embodiment, in some embodiments the ablation device 1230 may be integrated into the exterior surface of the fluid delivery element 1220.

The ablation device 1230 preferably includes a plurality of electrodes 1232 positioned over an exterior surface of the fluid delivery element 1220 (which is preferably located within the ablation device 1230). The electrodes 1232 may be used to deliver ablation energy (e.g., RF, DC, RF and DC, etc.) as described in connection with the other illustrative embodiments described herein.

In the depicted embodiment, the electrodes 1232 are provided in a series of circumferential rings 1233 distributed along the length of the ablation device 1230 (where the length is determined relative to the longitudinal axis 1201). The electrodes 1232 may, however, be distributed in a wide variety of patterns, etc. such that energy delivery can be effected in a selected manner.

In some embodiments, the plurality of electrodes may be distributed over the ablation device 1230 such that the number of electrodes 1232 per unit length of the ablation device 1230 decreases when moving distally along the direction of the longitudinal axis 1201. One illustrative embodiment of a distribution such as that is depicted in FIG. 15A, where the number of electrodes 1232 in each of the rings 1233 decreases when moving distally along the ablation device 1230 (where, e.g., the first (most proximal) ring 1233 may include 7-8 electrodes, the second ring may include 3-4 electrodes, the third ring may include 2-3 electrodes, and the distal-most ring may include 1-2 electrodes).

Another optional feature depicted in connection with the ablation device 1230 is that the ablation device, which includes a proximal end (the end nearest the distal end 1203 of the sheath 1202) and a distal end (the end furthest from the distal end 1203 of the sheath 1202), may preferably expand to a smaller size radially proximate the distal end of the ablation device 1230 and a larger size radially proximate the proximal end of the ablation device 1230 (where "radially" is determined relative to the longitudinal axis 1201). In other words, the distal portion of the ablation device 1230 may be narrower, smaller, etc. than the proximal portion of the ablation device 1230. Such a profile may, for example, be well-suited to use in narrowing passageways in a body.

Another optional feature depicted in connection with the embodiment of FIGS. 15A-15C is that the fluid delivery element 1220 and the ablation device 1230 may preferably be expandable from a compact configuration in which they are contained in a sheath lumen 1204 located in the sheath 1202 (see, e.g., FIG. 15C) to an enlarged configuration in which the fluid delivery element 1220 and the ablation device 1230 comprise radial dimensions (relative to the longitudinal axis 1201) that are larger than a radial dimension of the sheath lumen 1204. That expansion may be inherent, i.e., the fluid delivery element 1220 and/or the ablation device 1230 may expand when not constrained within the lumen 1204 (through the use of resilient materials, shape memory materials, etc.). In other embodiments, the expansion may be caused, at least in part, by fluid pressure from the fluid delivered into the fluid delivery element 1220.

The system 1200 of FIGS. 15A-15C may also include, in some embodiments, a fluid return lumen that can be used to remove fluid delivered through the fluid delivery element 1220. In some embodiments, the fluid return lumen may preferably include, as described herein, a return port proximate the distal end 1203 of the sheath 1202.

Although not depicted in FIGS. 15A-15C, the system 1200 may also preferably include an energy source operably connected to the plurality of electrodes 1232 through one or more conductors extending through the sheath 1202 (with the conductors in/attached to the sheath 1202 and/or catheter 1240). These components are, however, optional in some systems because they may be re-used with different ablation devices and related components described as a part of the system 1200. The energy source, where provided, may be in the form of, e.g., a DC electrical source, an RF energy source, an ultrasonic energy source, a microwave energy source, a vibration energy source, a laser, and/or a combination of any two or more thereof.

Although not depicted in FIGS. 15A-15C, the system 1200 may also preferably include a temperature sensing system as described herein. In some embodiments, the system may include a temperature sensor located proximate the distal end 1203 of the sheath 1202. Temperature sensors may, in some embodiments, be provided (in place of or in addition to placement on the sheath) on the ablation device 1230, fluid delivery device 1220, catheter 1240, combinations of two or more thereof, etc.

In some embodiments of the illustrative system depicted in FIGS. 15A-15C, the fluid delivery device 1220 and the ablation device 1230 are located at a distal end of a catheter 1240. The catheter 1240, the fluid delivery device 1220, and the ablation device 1230 are located within a sheath lumen 1204 in the sheath 1202 and movable distally along the longitudinal axis 1201 within the sheath lumen 1204. The fluid delivery element 1220 and the ablation device 1230 are preferably expandable from a compact configuration in which they are contained in the sheath lumen 1204 (see, e.g., FIG. 15C) to an enlarged configuration in which the fluid delivery element 1220 and the ablation device 1230 comprise radial dimensions relative to the longitudinal axis 1201 that are larger than a radial dimension of the sheath lumen 1204. In still further embodiments, the sheath 1202 may be positioned in a working channel of a bronchoscope 1205.

In one or more embodiments that includes circulating a fluid within a body cavity, the flow rate of the fluid may be any rate sufficient to circulate the fluid. Preferably, the lower end of the flow rate may be, e.g., 0.5 cubic centimeter per minute (cc/min) or higher, possibly 1 cc/min or higher, 5 cc/min or higher, etc. At the upper end, the flow rate may be 500 cc/min or lower, possibly 100 cc/min. or lower, 50 cc/min. or lower, etc. One example of a potentially suitable flow rate may be 10-20 cc/min. In some embodiments, any volume of fluid sufficient to transfer energy from the electrode(s) to the body cavity wall may be used. In some embodiments, dynamic algorithm based matching of inflow and outflow pumps based on temperature, pressure sensor information, electrogram information, direct visualization, etc. may be used.

In the present disclosure, a relatively high power level (e.g. higher than what may be used with cardiac ablation) may be used for ablation. For example, using relatively high power and relatively high fluid flow rates may reduce Ohmic heating and may increase conductive heating, which may allow ablation of the bronchial smooth muscle without adversely affecting the endothelium.

In one or more embodiments of the systems and methods described herein, a wide variety of energy modes or types may be used. For example, the energy provided to the walls of a body cavity (e.g., proximate the smooth muscle tissue to be impaired) may include, but is not limited to radiofrequency energy, ultrasound, microwave, vibration, alternating current, direct current, phasic direct current, and/or laser. In some embodiments that employ ultrasound or microwave energy, the fluid used may include, but is not limited to, a viscous or oil-based substance that may then be flushed out and removed. Examples of some potentially suitable substances include but are not limited to: mineral oil, caster oil, pine oil, emulsions of bronchodilatory and anti-inflammatory agents etc The systems and/or methods described herein may also involve a combination of vibration energy with another mode of energy. The ratio of each energy or ablation modality can potentially be manually or automatically adjusted based on, e.g., the cavity size and/or thickness of the smooth muscle layer. For example, ultrasound visualization may be used to determine tissue characteristics and that visualization may be performed either in conjunction with ultrasound-based ablation or as a stand-alone imaging tool along with the other modes of ablation energy delivery as described herein.

Vibration may have well established effects on transmembrane conduction. In some embodiments, for example, vibration produced via a (nitinol) sheath or balloon may produce some endothelial damage, but while not wishing to be bound by theory, it is believed that the effects on the smooth muscle tissue may be more profound. In some embodiments, for example, a nitinol sheath (or balloon) to be vibrated may have been conformed to the shape of the body cavity (e.g., bronchial airway, etc.) and may be used.

In one or more embodiments, vibration may be used as the energy provided to an ablation site and may be applied to, for example, a fixed column of fluid. In some embodiments, for example, a fluid may be delivered through the fluid delivery lumen to a body cavity to form a fixed column of fluid to which vibrational energy may be applied to effect smooth muscle tissue.

If used, ultrasound or other vibrational energy may be delivered from variable locations that may be static or dynamic within the body cavity. For example, ultrasonic energy may potentially be focused electronically, an ultrasound transducer may be moved, rotated, etc., different fluids having different acoustic properties may be used to change energy delivery profiles, etc.

In some embodiments, a conformable sheath or other structure may be used that can selectively deliver both vibration energy (e.g., ultrasonic, etc.) and other modes of energy (e.g., RF, DC, pressure, etc.). Such a device may potentially simultaneously and/or sequentially vibrate and emit one or more other modes of energy to the tissue lining a body cavity.

In one or more embodiments, focused ultrasound ablation energy may be delivered from a transducer placed between two expansion devices. In such a system, multiple options for focusing the ultrasonic energy may be available. For example, the electronics of the transducer itself may be used, the distance between the two expansion devices may be adjusted, etc. Further, the substance or substances used to fill the expansion devices and/or the body cavity located between the expansion devices may be selected based on acoustic characteristics. For example, varying these substances may provide a relative acoustic impedance mismatch that can be manipulated utilizing feedback from the modalities described herein to judge adequate lesion formation.

Electrolysis may be more potent in affecting cells that have, for example, an ionically active membrane such as cardiac myocytes, smooth muscle cells, etc., as well as actively dividing cells, such as tumor cells. In one or more embodiments of the present disclosure, the sheath (or catheter or bronchoscope) may be coated with a dielectric material and may be used as a direct current ablation surface to preferentially affect those types of cells.

In one or more embodiments, a method of electrolytic ablation may include using a device that includes a virtual electrode and optionally wherein direct current energy is used at higher levels than are generally thought permissible for the heart. In some embodiments, a surface pad or electrode could be placed on the same side of a body as the lung to be ablated in order to minimize energy transfer to the heart. While higher energies (e.g., DC energies) may cause heat and destruction of the endothelium as well as smooth muscle tissue (as may be useful to treat for COPD), the lower energy may be used more constantly and may be electrolytic ablation that will affect the smooth muscles. In some embodiments, a fluid (e.g., saline or other solution) may carry the direct current energy producing electrolysis and may also actually seep into the smooth muscle cells preferentially.

In one or more embodiments, a sheath may also be used as a conduit for tools useful in, for example, airway diagnosis, sampling, and/or treatment. For example, a split sheath or multi-layered sheath may, in some embodiments, be located over an ultra-thin bronchoscope, left in place after the bronchoscope is removed, and used as a passageway to the lesion of interest. Alternately, the sheath itself may include a camera and/or a light in addition to or instead of using the bronchoscope.

Regardless of the specific types of energy delivered, dynamic algorithms and timing sequences of ablation can be made dependent on, e.g., the pattern of heating observed and/or the presence or absence of smooth muscle relaxation or contraction in response to the energy delivery. The selected energy delivery may, in some instances, be based on direct visualization of the internal surfaces of the body cavity to which the energy is delivered.

Other characteristics may also be monitored to assist with the selection of energy delivery parameters, e.g., the use of pressure sensors to measure the extent of smooth muscle tone around the body cavity (e.g., bronchus, etc.). Once the tone decreases below a selected lower level (for example <10% of baseline), energy delivery can be terminated, changed, etc. Alternatively, if smooth muscle tone is noted to increase during the selected energy delivery, the delivery may be stopped and one or more other modes of energy may be delivered as described herein. In another example, other substances, e.g., pharmacological agents (e.g. a bronchodilatory substance), etc. may be delivered to achieve the desired effects on the smooth muscle tissue.

One or more embodiments of the systems and methods described herein may include a wide variety of additional features. For example, a sheath (e.g., an ultra-thin bronchoscope) may include one or more sensors that may aid in, for example, tracking, navigation and/or steering (e.g., systems currently used for intracardial navigation may include, for example, LocaLisa (Medtronic), Nav-X (En Site), and Carto-Merge (Biosense Webster)). In some embodiments, one or more sensors may also be used to, for example, track an ablation electrode location, which may be particularly useful if the electrode is moving through a column of fluid (e.g., saline). The fluid may itself serve as an electrode sensor for localization during electrolysis.

The systems may be used with or without an imaging device (e.g., a bronchoscope, endoscope, etc.) and, for example, a sheath used to deliver other components may itself serve as a visualizing apparatus, either with direct visualization or with the use of electrogram and other sensor based navigation and/or visualization as described herein.

In one or more embodiments of the systems and methods described herein, one or more optional navigation and steering sensors may be used. One or more optional navigation and steering sensors may include, but are not limited to, impedance sensors, electrogram sensors, pressure sensors, wind sensors (e.g., an anemometer), humidity sensors, carbon dioxide sensors, temperature sensors, ultrasound sensors, etc.

For example, one or more embodiments of the systems and methods described herein may include one or more impedance sensors that may aid navigation and/or steering of a device within a body cavity (e.g., a bronchus, a bronchiole, etc.). In some embodiments, an impedance sensor may be capable of distinguishing between a high impedance material (e.g., air) and a low impedance material (e.g., body tissues including a bronchus, lung parenchyma, mapped lesions in the lung, etc.).

One or more embodiments of the present disclosure one or more electrogram sensors may aid navigation and/or steering of a device. For example, around an expansion device or on a deflectable catheter, the electrogram sensors may detect electrical signals primarily from viable smooth muscle tissue. These electrograms can be measured at baseline and continuously measured during ablation. Introduction in the electrogram amplitude, fragmentation of the electrogram, suppression of "tachycardia" from rapid firing and thus rapid electrograms can potentially be used to diagnose specific sites requiring targeted ablation, as well as to measure an endpoint for the ablation procedure itself.

The electrograms may also guide navigation. For example, the front end of the device, if near field electrograms are noted, is likely in contact with the wall rather than the lumen itself thus allowing appropriate manipulation of the device.

In some embodiments of the systems and/or methods described herein, one or more pressure sensors may aid navigation and/or steering of a device. Similarly, steering of the device to reduce the likelihood of perforation and/or for determining endpoints for ablation can potentially be accomplished using a pressure sensor. The pressure sensed will depend on the size of the body cavity and the smooth muscle tone. When high pressure is detected during navigation, the device can be manipulated accordingly to avoid perforation. Similarly, increasing pressure during energy delivery suggests either migration of the device or impending event (e.g., a bronchospasm), and that information could then be used to increase energy delivery and/or manipulate the device, etc.

In some embodiments, a navigation and/or steering sensor may include one or more wind sensors or an anemometer, which may detect wind velocity within a lumen. For example, one or more wind sensors or an anemometer may aid in navigation by measuring the direction and velocity of airflow within the body cavity. In embodiments in which a bronchoscopy-based ablation device includes an occlusion device that is secured in, for example, a bronchus, a scope or sheath may include one or more ports to allow air movement through breathing.

In some embodiments, a navigation and/or steering sensor may include one or more humidity sensors. For example, water vapor may be detected with a sensor (or a reagent on a sensor) that may be transduced electrically. Moisture may be detected throughout a body cavity (e.g., a bronchus, etc.) and contact with tissue may be detected with a humidity sensor, which may aid in steering. Various airway branches (e.g., bronchi, etc.) may include differing amounts of moisture that may be detected with one or more humidity sensors.

In some embodiments, a navigation and/or steering sensor may include one or more carbon dioxide sensors which may aid in navigation and/or steering. A relatively low reading of carbon dioxide (or no reading at all) concentration may indicate an airway wall or other tissue. However, a relatively high reading of carbon dioxide concentration may indicate that the sensor (e.g., the sheath or scope tip including the sensor) may be in the airway.

In some embodiments, a navigation and/or steering sensor may include one or more temperature sensors through the use of thermography. For example, a thermistor on, for example, a sheath or bronchoscope tip may allow distinguishing between a circulating air temperature and a tissue (e.g., bronchus, etc.) temperature to aid in navigation. In addition, circulating air that may be warmer (or cooler) than body temperature may also allow detection of temperature changes due to circulation from breathing.

In one or more embodiments, a temperature gradient monitor may be included, for example, in embodiments in which the electrode is a "floating" electrode, or one that moves along a column of fluid (e.g., a conductive fluid such as saline, etc.). The floating probe may be capable of advancing deeper into the bronchial system within the virtual electrode and back. In some embodiments, a floating probe may also be deflected closer to the wall and/or further from the wall. Deflecting the floating probe closer to and further from the wall back and forth may be tracked in real-time and by observing the difference in temperature further from the wall and closer to the wall, from which a gradient may be calculated. It may be possible, in some embodiments, that from prior estimation of luminal size an inverse solution may be applied to calculate the temperature at the surface.

In some embodiments, a navigation and/or steering sensor may include one or more ultrasound devices and/or sensors. For example, using a linear phased array probe (e.g., single, dual, multi-phased, etc.) with limited elements on the tip (e.g., mostly for Doppler but may obtain a B mode image or an M mode image in one or two planes, etc.) to determine whether tissue is out in front or on the sides of the tip.

In addition to use in the bronchial tree, the systems described herein could potentially be used in various locations including cardiac applications; for example, placing pacing leads through the veins and in the pericardial space. The systems could also potentially be used to ablate the cardiac nerve, coronary vessels, in autonomic or ventriculo-fibrillation ablation, in central nervous system (CNS) applications, in gastrointestinal (GI) motility disorders, sphincter disorders, and urologic applications.

In some embodiments used to treat bronchial cavities, the systems and methods described herein may be used to target the vagal afferents, as well as possibly the sympathetic efferents The sympathetic efferents that supply the bronchus muscle are distinct from the efferents that go to the heart and travel along the bronchi, bronchial arteries and pulmonary arterials.

The bronchial afferents—vagal afferents are distributed via several pulmonary plexuses. Some of these supply the mucosa, and may potentially be useful to reduce coughing in people with intractable coughs, etc.

As for the plexuses related to the bronchial muscle, the bronchial afferents—vagal afferents encircle the myocytes and end in these tendrils (that are referred to as muscle spindles). These muscle spindles are located fairly superficially and are influenced by stretching. The intra-alveolar connective tissue also has some plexuses visualized as knob-like endings and with terminals or myocytes and these are the ones that may be involved with allowing the hering-breuer reflex to occur.

In connection with the systems and methods described herein, stretching the muscle spindles and smooth muscle segments alone or in combination with the delivery of energy as described herein may be used to ablate or modify the vagal afferents and possibly sympathetic efferents to treat conditions such as, e.g., asthma, chronic cough, etc. without necessarily destroying the bronchial muscle. The stretching may be accomplished by using an expansion device as described herein and/or delivering fluid to a selected, enclosed volume under pressure to stretch the surrounding bronchial tissue.

The following documents may provide further description of various components that may be used in connection with the systems and methods described herein: U.S. Pat. No. 6,493,589 (Medhkour et al.); U.S. Pat. No. 6,539,265 (Medhkour et al.) U.S. Pat. No. 7,184,827 (Edwards); U.S. Pat. No. 7,264,002 (Danek et al.); U.S. Pat. No. 7,027,869 (Danek et al.); U.S. Pat. No. 7,273,055 (Danek et al.); U.S. Pat. No. 7,198,635 (Danek et al.); U.S. Pat. No. 6,634,363 (Danek et al.); U.S. Pat. No. 6,580,938 (Acker); U.S. Pat. No. 5,259,366 (Reydel et al.); U.S. Pat. No. 6,569,085 (Kortenbach et al.); U.S. Pat. No. 6,852,078 (Ouchi); and U.S. Pat. No. 7,233,820 (Gilboa); U.S. Pat. App. Pub. No. 2006/0149134 (Soper et al.); 2005/0038408 (von Segesser); 2007/0239138 (Lawrence et al.); 2006/0184016 (Glossup); 2007/0293721 (Gilboa); Cox et al. "Radiofrequency ablation of airway smooth muscle for sustained treatment of asthma: preliminary investigations," *Eur. Respir. J.*, 2004, 24: 659-663; Cox et al., "Bronchial Thermoplasty for Asthma," *Am. J Respir. Crit. Care Med.*, 2006, 173: 965-969; Hinz et al., "Electrolytic Ablation is as Effective as Radiofrequency Ablation in the Treatment of Artificial Liver Metastases in a Pig Model," *J. Surg. Onc.*, 2008, 98: 135-138; and Tsushima et al., "Bronchoscopy-guided radiofrequency ablation as a potential novel therapeutic tool," *Eur. Respir. J.*, 2007, 29: 1193-1200.

The complete disclosure of the patents, patent documents, and publications cited herein are incorporated by reference in their entirety as if each were individually incorporated.

Illustrative embodiments have been discussed and reference has been made to possible variations within the scope of this disclosure. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A smooth muscle tissue impairment system comprising:
an elongated sheath comprising a proximal and a distal end, a distal end opening, and a longitudinal axis extending between the proximal end and the distal end;
a fluid supply apparatus comprising a pump;
an ablation apparatus comprising:
    an ablation device extending through the elongated sheath, wherein the ablation device can be moved distally and proximally relative to the elongated sheath, the ablation device comprising a catheter with a distal tip moveable through the distal end opening of the sheath;
    wherein the ablation device includes a delivery lumen extending therethrough, the delivery lumen having a delivery port at the distal tip of the catheter moveable through the distal end opening of the sheath, and wherein fluid supplied by the fluid supply apparatus is delivered through the delivery lumen and out through the delivery port, whereby fluid delivered through the delivery lumen and the delivery port comes into contact with tissue when the delivery port is positioned adjacent to the tissue;
    wherein the ablation device includes a return lumen extending therethrough, the return lumen comprising a return port proximate the distal end of the ablation device and in fluid communication with the delivery port such that the fluid delivered out through the delivery port can be withdrawn through the return port and the return lumen; and
    wherein the ablation device includes an electrode attached to the distal tip of the catheter moveable through the distal end opening of the sheath; and
an energy source operably connected to the electrode through a conductor extending through the ablation device, such that the electrode can supply energy from the energy source;
    wherein, the electrode is positioned on the distal tip of the catheter adjacent to the delivery port on the distal tip of the catheter such that energy supplied by the electrode is transferred through the fluid delivered out through the delivery port, whereby energy supplied by the electrode is transferred through the fluid to tissue when the delivery port is positioned adjacent to the tissue.

2. A system according to claim 1, wherein at least a portion of fluid delivered to an enclosed volume through the delivery port of the delivery lumen can be removed from the enclosed volume through the return lumen.

3. A system according to claim 1, wherein the system further comprises an expansion device on an exterior surface of the elongated sheath, wherein the expansion device comprises a delivery configuration in which the expansion device is unexpanded and an expanded configuration in which the expansion device is expanded to increase its size as compared to the delivery configuration.

4. A system according to claim 1, wherein the energy source comprises two or more of: a DC electrical source, an RF energy source, an ultrasonic energy source, a microwave energy source, a vibration energy source, a laser.

5. A system according to claim 1, further comprising a temperature sensing system comprising a temperature sensor located proximate the distal end of the elongated sheath.

6. A system according to claim 1, wherein the fluid supply apparatus comprises a fluid reservoir and a peristaltic pump.

7. A system according to claim 1, wherein the energy source comprises a DC electrical source.

8. A system according to claim 1, wherein the energy source comprises an RF energy source.

9. A system according to claim 1, wherein the energy source comprises an ultrasonic energy source.

10. A system according to claim 1, wherein the energy source comprises a microwave energy source.

11. A system according to claim 1, wherein the energy source comprises a vibration energy source.

12. A system according to claim 1, wherein the energy source comprises a laser.

13. A system according to claim 3, wherein the expansion device on the exterior surface of the elongated sheath comprises a balloon.

* * * * *

UNITED STATES PATENT AND TRADEMARK OFFICE
CERTIFICATE OF CORRECTION

| | | |
|---|---|---|
| PATENT NO. | : 10,828,462 B2 | Page 1 of 1 |
| APPLICATION NO. | : 13/375698 | |
| DATED | : November 10, 2020 | |
| INVENTOR(S) | : Craig E. Daniels and Samuel J. Asirvatham | |

It is certified that error appears in the above-identified patent and that said Letters Patent is hereby corrected as shown below:

On the Title Page

Item (73) "Sanovas Intellectual Property, LLC" should be changed to --Mayo Foundation for Medical Education and Research--

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*